US009409146B2

(12) United States Patent
Frangione et al.

(10) Patent No.: US 9,409,146 B2
(45) Date of Patent: Aug. 9, 2016

(54) METHOD FOR TREATING AMYLOID DISEASE

(71) Applicant: New York University, New York, NY (US)

(72) Inventors: Blas Frangione, New York, NY (US); Einar M. Sigurdsson, Scarsdale, NY (US); Thomas Wisniewski, Staten Island, NY (US); Jorge Ghiso, Elmhurst, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/655,234

(22) Filed: Oct. 18, 2012

(65) Prior Publication Data

US 2013/0045216 A1 Feb. 21, 2013

Related U.S. Application Data

(62) Division of application No. 12/366,126, filed on Feb. 5, 2009, now Pat. No. 8,318,175, which is a division of application No. 10/540,294, filed as application No. PCT/US03/40744 on Dec. 18, 2003, now abandoned.

(60) Provisional application No. 60/434,736, filed on Dec. 19, 2002.

(51) Int. Cl.

| | |
|---|---|
| *A61K 38/17* | (2006.01) |
| *B01D 61/00* | (2006.01) |
| *A61K 39/395* | (2006.01) |
| *A61P 25/28* | (2006.01) |
| *B01J 20/28* | (2006.01) |
| *A61K 31/739* | (2006.01) |
| *A61K 38/30* | (2006.01) |
| *A61K 38/38* | (2006.01) |
| *A61K 38/39* | (2006.01) |
| *A61K 38/55* | (2006.01) |
| *B01J 20/32* | (2006.01) |
| *B01J 20/34* | (2006.01) |
| *A61M 1/34* | (2006.01) |

(52) U.S. Cl.
CPC ......... *B01J 20/28033* (2013.01); *A61K 31/739* (2013.01); *A61K 38/1709* (2013.01); *A61K 38/30* (2013.01); *A61K 38/38* (2013.01); *A61K 38/39* (2013.01); *A61K 38/55* (2013.01); *B01J 20/3206* (2013.01); *B01J 20/3208* (2013.01); *B01J 20/3217* (2013.01); *B01J 20/3219* (2013.01); *B01J 20/3246* (2013.01); *B01J 20/3248* (2013.01); *B01J 20/3274* (2013.01); *B01J 20/345* (2013.01); *B01J 20/3475* (2013.01); *A61M 1/34* (2013.01); *B01J 2220/58* (2013.01); *B01J 2220/66* (2013.01)

(58) Field of Classification Search
USPC ............... 210/645; 514/1.1, 17.8; 424/172.1
See application file for complete search history.

(56) References Cited

U.S. PATENT DOCUMENTS

| | | |
|---|---|---|
| 4,409,105 A | 10/1983 | Hayashi et al. |
| 4,770,774 A | 9/1988 | Ida et al. |
| 5,216,127 A | 6/1993 | Hirai et al. |
| 5,434,170 A | 7/1995 | Andrulis, Jr. |
| 5,604,102 A | 2/1997 | McConlogue et al. |
| 5,679,775 A | 10/1997 | Boos et al. |
| 5,817,528 A | 10/1998 | Bohm et al. |
| 5,948,763 A | 9/1999 | Soto-Jara et al. |
| 6,274,615 B1 | 8/2001 | Pappolla et al. |
| 6,713,450 B2 | 3/2004 | Frangione et al. |
| 7,195,761 B2 | 3/2007 | Holtzman et al. |
| 7,427,655 B2 | 9/2008 | Frangione et al. |
| 7,479,482 B2 | 1/2009 | Frangione et al. |
| 7,700,107 B2 | 4/2010 | Frangione et al. |
| 7,732,568 B2 | 6/2010 | Mattner |
| 7,892,545 B2 | 2/2011 | Holtzman et al. |
| 7,935,252 B2 | 5/2011 | Mattner |
| 7,935,348 B2 | 5/2011 | Mattner et al. |
| 8,591,894 B2 | 11/2013 | Holtzman et al. |
| 2002/0009445 A1 | 1/2002 | Du et al. |
| 2002/0037290 A1 | 3/2002 | Armen |
| 2004/0081657 A1 | 4/2004 | Schenk |
| 2006/0039906 A1 | 2/2006 | Holtzman et al. |
| 2009/0004210 A1 | 1/2009 | Mattner et al. |
| 2009/0104211 A1 | 4/2009 | Mattner et al. |
| 2009/0175853 A1 | 7/2009 | Frangione et al. |

(Continued)

FOREIGN PATENT DOCUMENTS

| | | |
|---|---|---|
| EP | 0236509 A1 | 9/1987 |
| JP | 6-104122 B2 | 12/1994 |

(Continued)

OTHER PUBLICATIONS

DeMattos et al. Peripheral anti-A beta antibody alters CNS and plasma A beta clearance and decreases brain A beta burden in a mouse model of Alzheimer's disease. Proc Natl Acad Sci U S A. Jul. 17, 2001;98(15):8850-5. Epub Jul 3, 2001.*

Kojima. High-performance immunoaffinity chromatography, an immunoaffinity membrane for selective removal of plasma components, and safety evaluation of the latter system. J Biochem Biophys Methods. Oct. 30, 2001;49(1-3):241-51.*

Carro et al., Serum insulin-like growth factor I regulates brain amyloid-beta levels, Nat Med, vol. 8, pp. 1390-1397, 2002.

(Continued)

*Primary Examiner* — Gregory S Emch
(74) *Attorney, Agent, or Firm* — Troutman Sanders LLP

(57) ABSTRACT

Disclosed herein are methods for treating amyloid disease in humans by clearing amyloid peptides from one or more bodily fluids such as, e.g., blood, of a patient. In particular, the methods are based on the administration of compounds capable of binding to amyloid-beta (Aβ) or on dialysis of blood or plasma exchange in order to remove Aβ peptides from the blood circulation, and/or brain or other affected organs.

3 Claims, 4 Drawing Sheets

(56) References Cited

U.S. PATENT DOCUMENTS

| | | |
|---|---|---|
| 2011/0015131 A1 | 1/2011 | Mattner |
| 2011/0166327 A1 | 7/2011 | Mattner et al. |
| 2011/0201987 A1 | 8/2011 | Mattner et al. |

FOREIGN PATENT DOCUMENTS

| | | |
|---|---|---|
| JP | 9-508976 | 9/1997 |
| JP | 2003-523764 A | 8/2003 |
| WO | WO 87/01597 A1 | 4/1987 |
| WO | WO 95/31727 A1 | 11/1995 |
| WO | WO 95/31966 | 11/1995 |
| WO | WO 96/39834 | 12/1996 |
| WO | WO 98/39653 | 3/1998 |
| WO | WO 98/15179 | 4/1998 |
| WO | WO 99/27944 | 6/1999 |
| WO | WO 99/27949 | 6/1999 |
| WO | WO 00/72800 | 12/2000 |
| WO | WO 01/62801 A2 | 8/2001 |
| WO | WO 01/90182 | 11/2001 |
| WO | WO 02/11669 | 2/2002 |
| WO | WO 03/051374 | 6/2003 |
| WO | WO 2005/025651 A1 | 3/2005 |

OTHER PUBLICATIONS

Castillo G.M. Perlecan binds to the beta-amyloid proteins (A beta) of Alzheimer's disease, accelerates A beta fibril formation, and maintains A beta fibril stability, J Neurochem., vol. 69(6), pp. 2452-2465, 1997.

Demattos et al., Clusterin promotes amyloid plaque formation and is critical for neuritic toxicity in a mouse model of Alzheimer's disease, Proc Natl Acad Sci USA, vol. 99, pp. 10843-10848, 2002.

Findeis MA et al., Approaches to discovery and characterization of inhibitors of amyfoid beta-peptide polymerization, Biochim Biophys Acta, vol. 1502, pp. 76-84, 2000.

Frenkel et al., High affinity binding of monoclonal antibodies to the sequential epitope EFRH of beta-amyloid peptide is essential for modulation of fibrillar aggregation, J Neuroimmunol, vol. 95, pp. 136-142, 1999.

Ghersi-Egea et al., Fate of cerebrospinal fluid-borne amyloid beta-peptide: rapid clearance into blood and appreciable accumulation by cerebral arteries, J Neurochem, vol. 67(2), pp. 880-883, 1996.

Ghiso et al., The cerebrospinal-fluid soluble form of Alzheimer's amyloid beta is complexed to SP-40,40 (apolipoprotein J),an inhibitor of the complement membrane-attack complex, Biochem J, vol. 293, pp. 27-30, 1993.

Ghiso et al., Unifying features of systemic and cerebral amyloidosis, Mol Neurobiol.,vol. 8, pp. 49-64, 1994.

Ghiso et al. Alzheimer's soluble amyloid β is a normal component of human urine, FEBS Letters, vol. 408, pp. 105-108, 1997.

International Search Report for PCT/US03/40744, dated Jan. 26, 2006.

Jarrett et al. The carboxy terminus of the beta amyloid protein is critical for the seeding of amyloid formation: implications for the pathogenesis Alzheimer's disease, Biochemistry, vol. 32, pp. 4693-4697, 1993.

Jarrett et al., Seeding one-dimensional crystallization of amyloid: a pathogenic mechanism in Alzheimer's disease and scrapie? Cell, vol. 73, pp. 1055-1058, 1993.

Ji et al., Amyloid beta 40/42 clearance across the blood-brain barrier following intraventricular injections in wild-type, apoE knock-out and human apoE3 or E4 expressing transgenic mice, . Journal of Alzheimer's Disease, vol. 3, pp. 23-30, 2001.

Jordan J., Isoform-Specific Effect of Apolipoprotein E on Cell Survival and beta-Amyloid-Induced Toxicity in Rat Hippocampal Pyramidal Neuronal Cultures, J. Neurosci., vol. 18, No. 1, pp. 195-204, 1998.

Koudinov et al., the soluble form of Alzheimer's amyloid beta protein is complexed to high density lipoprotein 3 and very high density lipoprotein in normal human plasma, Biophys Res Commun, vol. 205, No. 2, pp. 1164-1171, 1994.

Matsubara, et al. Characterization of Apolipoprotein J-Alzheimer's Aβ Interaction. The Journal of Biological Chemistry, vol. 270, No. 13, pp. 7563-7567, 1995.

Matsuoka, Y. Novel Therapeutic Approach for the Treatment of Alzheimer's Disease by Peripheral Administration of Agents with an Affinity to beta-Amyloid, J. Neurosci, vol. 23, No. 1. pp. 29-33, 2003.

Pepys et al., Targeted Pharmacological Depletion of Serum Amyloid P Component for Treatment of Human Amyloidosis, Nature, vol. 417, pp. 254-259, 2002.

Permanne et al, Detection of apolipoprotein E/Dimeric Soluble Amyloid J3 Complexes in Alzheimer's Disease Brain Supernatants, Biochemical and Biophysical Research Communications, vol. 240, pp. 715-720, 1997.

Seubert et al., Mutation of the beta-amyloid precursor protein in familial Alzheimer's disease increases beta-protein production Nature, vol. 359, pp. 325-327, 1992.

Shibata et al., Clearance of Alzheimer's amyloid-ss(1-40) peptide from brain by LDL receptor related protein-1 at the blood-brain barrier, J Clin Invest, vol. 106, pp. 1489-1499, 2000.

Shoji et al., Production of the Alzheimer amyloid beta protein by normal proteolylic processing, Science, vol. 258, pp. 126-129, 1992.

Sigurdsson et al., In vivo reversal of amyloid-beta lessons in rat brain, J Neuropath Exp Neurol, vol. 59, pp. 11-17, 2000.

Sigurdsson et al., An Attenuated Immune Response Is Sufficient to Enhance Cognition in an Alzheimer's Disease Mouse Model Immunized with Amyloid-β Derivatives, The Journal of Neuroscience, vol. 24, pp. 6277-6282, 2004.

Soto et al., Beta-Sheet breaker peptides inhibit fibrillogenesis in a rat brain model of amyloidosis: implications for Alzheimer's therapy, Nat Med, vol. 4, pp. 822-826, 1998.

Vickers et al., A vaccine against Alzheimer's disease: developments to date, Drugs Aging, vol. 197(7), pp. 487-494, 2002.

Yliera et al., Method for treating amyloid disease, Biochem. Biophys. Res. Comm., vol. 200, pp. 1583-1588, 2002.

Wisniewski et al., Short Communication: Acceleration of Alzheimer's Fibril Formation by Apolipaprotein E In Vitro, American Journal of Pathology, vol. 145, No. 5, pp. 1030-1035, 1994.

Zlokovic et al. Brain uptake of circulating apolipoproteins J and E complexed to Alzheimer's amyloid beta, Biochem Biophys Res Commun, vol. 205, pp. 1431-1437, 1994.

Zlokovic et al., Glycoprotein 330/megalin: probable role in receptor-mediated transport of apolipoprotein J alone and in a complex with Alzheimer's disease amyloid? at the blood-brain and blood-cerebrospinal fluid barriers, Proc Natl Acad Sci USA, vol. 93, pp. 4229-4234, 1996.

Alberts, 1994, Molecular Biology of the Cell, pp. 104-111.

Cassel, et al, 2001, "Demography and Epidemiology of Age-Associated Neuronal Impairment", Functional Neurobiology of Aging, pp. 31-50.

Sen, 2003, "On-line immunoaffinity-liquid chromatography-mass spectrometry for identification of amyloid disease markers in biological fluids", Anal. Chem. 75, pp. 1196-1202.

Dodart et al, 2002, "Immunization reverses memory deficits without reducing brain amyloid-beta burden in Alzheimer's disease model", Nature Neuroscience 5, pp. 452-457.

Demattos et al, 2002, "Brain to Plasma Abeta efflux: a measure of brain amyloid burden in a mouse model of Alzheimer's Disease", Science vol. 295, pp. 2264-2267.

Wilcock et al, "Passive immunotherapy against Abeta in aged APP-transgenic mice reverses cognitive deficits and depletes parenchymal amyloid deposits in spite of increased vascular amyloid and microhemorrhage", Journal of Neuroinflammation 2004 1:24, pp. 1-11.

Freund J, "Antibodies in central nervous system", Journal of Experimental Medicine, Freund 51(6), 1930, pp. 889-902.

Horikoshi et al, "Abeta N-terminal-end specific antibody reduced beta-amyloid in Alzheimer-model mice", Biochemical and Biophysical Research Communications 325, 2004, pp. 384-387.

Kotilinek et al, "Reversible memory loss in a mouse transgenic model of Alzheimer's disease", The Journal of Neuroscience, 2002, 22(15), pp. 6331-6335.

Masliah et al, "Effects of alpha-synuclein immunization in a mouse model of Parkinson's disease", Neuron 46, 2005, pp. 857-868.

(56) References Cited

OTHER PUBLICATIONS

Wilcock et al, "Passive amyloid immunotherapy clears amyloid and transiently activates microglia in a transgenic mouse model of amyloid deposition", The Journal of Neuroscience 24(27), 2004, pp. 6144-6151.

Wilcock et al, "Intracranially administered anti-Abeta antibodies reduce beta-amyloid deposition by mechanisms both independent of and associated with microglial activation", The Journal of Neuroscience, 23(9), 2003, pp. 3745-3751.

Schenck et al, "Immunization with amyloid-beta attenuates Alzheimer-disease-like pathology in the PDAPP mouse", Nature 400, 1999, pp. 173-177.

Bard et al, "Peripherally administered antibodies agains amyloid beta-peptide enter the central nervous system and reduce pathology in a mouse model of Alzheimer disease", Nature Medicine 6(8), 2000, pp. 916-919.

Sperling et al, "Amyloid-related imaging abnormalities in patients with Alzheimer's disease treated with bapineuzumab: a retrospective analysis", Lancet Neurol. 11, 2012, pp. 241-249.

Alzforum. "Crenezumab Disappoints in Phase 2, Researchers Remain Hopeful" Alzheimer's Association International Conference (AAIC) Jul. 22, 2014. Retrieved online on Dec. 16, 2014 from: http://www.alzforum.org/news/conference-coverage/crenezumab-disappoints-phase-2-researchers-remain-hopeful.

Bruce-Keller, et al. "Concern over the amyloid vaccine: amyloid heterogeneity and Fc receptor signaling" Neurobiology of Aging 2002, 23:667-670.

Doody et al. "Phase 3 Trials of Solanezumab for Mild-to-Moderate Alzheimer's Disease" The New England Journal of Medicine 2014, 370(4):311-321.

Munch et al. "Alzheimer's vaccine: a cure as dangerous as the disease?" Journal of Neural Transmission 2002, 109:537-539.

Salloway et al. "Two Phase 3 Trials of Bapineuzumab in Mild-to-Moderate Alzheimer's Disease" The New England Journal of Medicine 2014, 370(4):322-333.

Golde, et al. "Quantitative and Mechanistic Studies of Aβ Immunotherapy" CNS & Neurological Disorders—Drug Targets 2009, 8:31-49.

* cited by examiner

SEQUENCE LISTING

```
<160> NUMBER OF SEQ ID NOS: 2

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 42
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

METHOD FOR TREATING AMYLOID DISEASE

CROSS-REFERENCE TO RELATED APPLICATIONS

This application is a divisional of U.S. patent application Ser. No. 12/366,126, filed Feb. 5, 2009, which is a divisional of U.S. patent application Ser. No. 10/540,294, filed Jun. 20, 2005, which is the U.S. National Stage of International patent application number PCT/US2003/040744, filed Dec. 18, 2003, which claims the benefit of U.S. provisional application No. 60/434,736, filed Dec. 19, 2002, all of which are hereby incorporated by reference in their entirety.

STATEMENT AS TO FEDERALLY SPONSORED RESEARCH

The United States Government has certain rights to this invention by virtue of funding reserved from Grant Nos. AG08721, AR02594, AG17617, AG05891, and AG20197 from the National Institutes of Health.

FIELD OF THE INVENTION

The present invention relates to methods for treating human amyloid disease. Specifically, this invention relates to methods of reducing the levels of amyloid-beta (Aβ) peptides in bodily fluids by, e.g., the administration of compounds capable of associating with Aβ, or the dialyzation of blood through a column or membrane to remove free Aβ.

BACKGROUND OF THE INVENTION

Amyloid disease (disorders of protein folding), or amyloidosis, is characterized by the accumulation of a peptide, including the Aβ peptide, existing as abnormal insoluble cross-β sheet fibrils or amyloid deposits in the affected organs. Amyloid diseases include, but are not limited to, Alzheimer's disease, type 2 diabetes, Huntington's disease, Parkinson's disease, and chronic inflammation. Amyloidosis is also a common and serious complication of long-term heamodialysis for end-stage renal failure. Amyloidosis—in which amyloid deposits are the direct cause of death—is responsible for about one per thousand of all deaths in developed countries.

Alzheimer's Disease (AD) is the most common form of late-life dementia in adults (Ghiso et al., Adv. Drug Deliv. Rev. 2002; 54(12):1539-51), constituting the fourth leading cause of death in the United States. Approximately 10% of the population over 65 years old is affected by this progressive degenerative disorder that is characterized by memory loss, confusion and a variety of cognitive disabilities.

Neuropathologically, AD is characterized by four major lesions: a) intraneuronal, cytoplasmic deposits of neurofibrillary tangles (NFT), b) parenchymal amyloid deposits called neuritic plaques, c) cerebrovascular amyloidosis, and d) synaptic and neuronal loss. One of the key events in AD is the deposition of amyloid as insoluble fibrous masses (amyloidogenesis) resulting in extracellular neuritic plaques and deposits around the walls of cerebral blood vessels. The major constituent of the neuritic plaques and congophilic angiopathy is Aβ, although these deposits also contain other proteins such as glycosaminoglycans and apolipoproteins.

Evidence that amyloid may play an important role in the early pathogenesis of AD comes primarily from studies of individuals affected by the familial form of AD (FAD) or by Down's syndrome. Down's syndrome patients have three copies of the APP gene and develop AD neuropathology at an early age (Wisniewski et al., Ann Neurol 1985; 17:278-282). Genetic analysis of families with hereditary AD revealed mutations in chromosome 21, near or within the Aβ sequence (Ghiso et al., Adv. Drug Deliv. Rev. 2002; 54(12):1539-51), in addition to mutations within the presenilin 1 and 2 genes. Moreover, it was reported that transgenic mice expressing high levels of human mutant APP progressively develop amyloidosis in their brains (Games et al., Nature 1995; 373:523-527). These findings appear to implicate amyloidogenesis in the pathophysiology of AD. In addition, Aβ fibrils are toxic to neurons in culture, and to some extent when injected into animal brains (Sigurdsson et al., Neurobiol Aging 1996; 17:893-901; Sigurdsson et al., J Neuropathol Exp Neurol 1997; 56:714-725).

Furthermore, several other pieces of evidence suggest that the deposition of Aβ is a central triggering event in the pathogenesis of AD, which leads subsequently to NFT formation and neuronal loss. The amyloid deposits in AD share a number of properties with all the other cerebral amyloidoses, such as the prion related amyloidoses, as well as the systemic amyloidoses. These characteristics are: 1) being relatively insoluble; 2) having a high degree of β-sheet secondary structure, which is associated with a tendency to aggregate or polymerize; 3) ultrastructurally, the deposits are mainly fibrillary; 4) the presence of certain amyloid-associating proteins such as amyloid P component, proteoglycans and apolipoproteins; and 5) deposits show a characteristic apple-green birefringence when viewed under polarized light after Congo red staining.

The same peptide that forms amyloid deposits in the AD brain was also found in a soluble form (sAβ) normally circulating in human body fluids (Seubert et al., Nature 1992; 359:325-327; Shoji et al., Science 1992; 258:126-129). sAβ was reported to pass freely from the brain to the blood (Ji et al., Journal of Alzheimer's Disease 2001; 3:23-30; Shibata et al., J Clin Invest 2000; 106:1489-99; Ghersi-Egea et al., J Neurochem 1996:67(2):880-3; Zlokovic et al., Biochem Biophys Res Commun 1994; 205:1431-1437), reported that the blood-brain barrier (BBB) has the capability to control cerebrovascular sequestration and transport of circulating sAβ, and that the transport of sAβ across the BBB was significantly increased in guinea pigs when sAβ was perfused as a complex with apolipoprotein J (apoJ). The sAβ-apoJ complex was found in normal cerebrospinal fluid (CSF; Ghiso et al., Biochem J 1993; 293:27-30; Ghiso et al., Mol. Neurobiol. 1994; 8:49-64) and in vivo studies indicated that sAβ is transported with apoJ as a component of the high density lipoproteins (HDL) in normal human plasma (Koudinov et al., Biochem Biophys Res Commun 1994:205:1164-1171). It was also reported by (Zlokovic et al., Proc Natl Acad Sci USA 1996; 93:4229-4234), that the transport of sAβ from the circulation into the brain was almost abolished when the apoJ receptor, gp330, was blocked. It has been suggested that the amyloid formation is a nucleation-dependent phenomena in which the initial insoluble "seed" allows the selective deposition of amyloid (Jarrett et al., Cell 1993; 73:1055-1058; Jarrett et al., Biochemistry 1993; 32:4693-4697).

Therapeutic strategies proposed for treating Alzheimer's disease and other amyloid diseases include the use of compounds that affect processing of the amyloid-β precursor protein (Dovey et al., J. Neurochem. 2001; 76:173-182), or that interfere with fibril formation or promote fibril disassembly (Soto et al., Nat Med 1998; 4:822-826; Sigurdsson et al., J Neuropath Exp Neurol 2000; 59:11-17; and Findeis M A., Biochim Biophys Acta 2000; 1502:76-84), as well as the administration of Aβ antibodies to disassemble fibrillar Aβ, maintain Aβ solubility and to block the toxic effects of Aβ (Frenkel et al., J Neuroimmunol 1999; 95:136-142). However, recently a Phase II clinical trial using a vaccination approach where Aβ1-42 was injected into individuals in the early stages of Alzheimer's disease was terminated because of cerebral inflammation observed in some patients.

Thus, despite these advances in the art, to date, there is no cure or effective therapy for reducing a patient's amyloid burden or preventing amyloid deposition in AD. Moreover, even the unequivocal diagnosis of AD can only be made after postmortem examination of brain tissues for the hallmark neurofibrillary tangles (NFT) and neuritic plaques. Thus, there exists a need in the art for developing effective methods for reducing a patient's amyloid burden.

SUMMARY OF THE INVENTION

The present invention is based, in part, on the discovery that amyloid diseases can be treated by removing Aβ peptides from a patient's bodily fluids. This can be accomplished by the administration of compounds that associate with Aβ in order to bind to free Aβ. Free Aβ can also be removed from a patient's bloodstream by dialysis. Both methods lead to an efflux of Aβ from the affected organs, resulting in the reduction of a patient's amyloid burden.

In one aspect the present invention provides a method for treating a patient suffering from an amyloid disease comprising administering to a patient in need of such treatment a therapeutically effective amount of a compound that is capable of associating with Aβ. In one embodiment, the compound binds to free Aβ present in the blood. In another embodiment, the compound binds to free Aβ present in the blood and in the brain. For example, the compound can be administered intravenously, and the transport of the compound into the brain enhanced by treating the patient in a manner so as to permeabilize the blood-brain-barrier. In a preferred embodiment, the blood-brain barrier is selectively permeabilized to compounds capable of associating with Aβ, including large protein ligands to Aβ and their complexes with Aβ.

In another aspect, the present invention provides a method for treating a patient suffering from an amyloid disease comprising filtering the blood of said patient through a filter, membrane or column with which is associated a compound capable of binding Aβ, thereby removing Aβ from the patient's blood.

These and other aspects of the present invention will be apparent to those of ordinary skill in the art in the following description, claims and drawings.

DETAILED DESCRIPTION OF THE INVENTION

Figure 1:
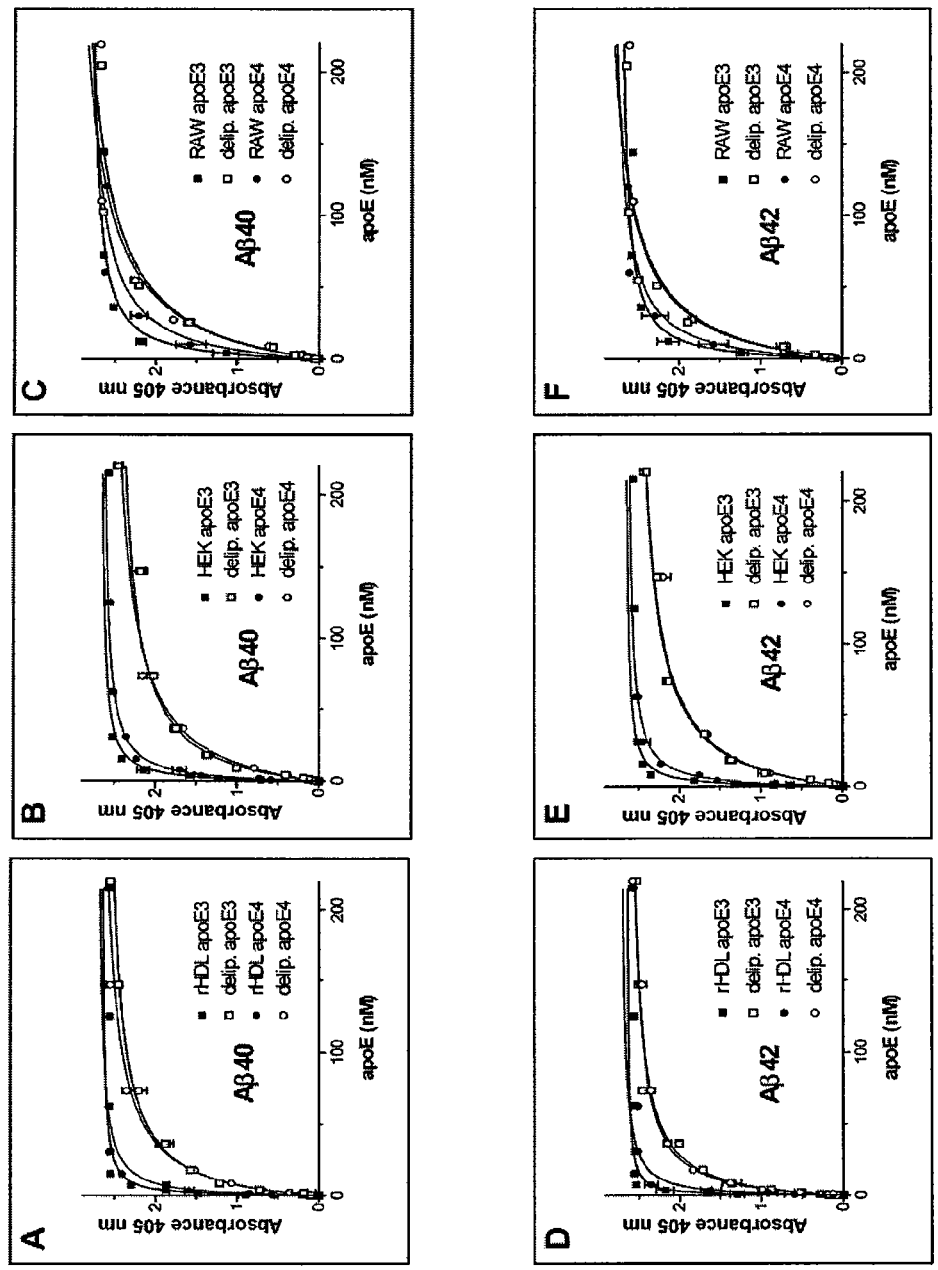
FIGS. 1A-1F show binding curves for the interactions of apoE3 and apoE4 with immobilized Aβ40 and Aβ42 peptides, FIGS. 1A-1C and 1D-1F, respectively. (A, D) Binding of Sf9-derived apoE3 and apoE4 in delipidated form or incorporated into r-HDLs. (B, E) Binding of HEK-derived apoE3 and apoE4 in delipidated form or in native HDL particles. (C, F) Binding of RAW-derived apoE3 and apoE4 in delipidated form or in native HDL-particles. Each point represents the mean (±standard deviation) of triplicates. See Example 1.

The present invention provides a method for removing the Aβ molecule from blood, from a blood component such as plasma or serum, and/or from another bodily fluid than blood.

In one embodiment, the Aβ peptide is removed from blood ex vivo with no use of any Aβ-ligand. For example, patient's blood can be subjected to convective dialysis, using an unidirectional membrane with a cut-off weight higher than that of Aβ, or to plasma exchange, thereby replacing plasma containing Aβ with Aβ-free plasma.

In another embodiment, the Aβ, present in the blood or blood component, is contacted ex vivo with an agent capable of associating with or binding to Aβ, i.e., an Aβ ligand. Such ligands include anti-Aβ antibodies or Aβ-binding antibody fragments, as well as the Aβ-associating agents described in Table 1. The ligand can be attached to a solid support or present in a dialysis compartment not allowing bound Aβ to flow back into the plasma compartment. For example, an Aβ-ligand attached to a solid support can be incorporated in a hemofiltration device or other device known in the art. In this embodiment, Aβ is "specifically removed", meaning that all or a portion of the amount of target molecules removed from the blood or blood component without the removal of other peptides, hormones or other blood constituents, and the patient is not exposed directly to the ligand by injection or other means.

Methods of ex vivo treatment include, but are not limited to, plasma perfusion, hemodialysis, and hemofiltration. The methods can be conducted on a continuous or batch basis. "Cleansed" blood or blood component may be returned to the patient concurrently with perfusion treatment or following perfusion treatment. The perfused blood or blood component may be supplemented or reconstituted with components from donated blood, artificial or synthetic components, therapeutic agents, or some combination thereof.

In yet another embodiment, the contacting between Aβ and an Aβ-ligand such as an anti-Aβ antibody or Aβ-binding fragment thereof, or one of the Aβ-associating agents described in Table 1, may take place in vivo after administering the Aβ-ligand to a patient. Typically, the ligand is administered in a manner so that it reaches the blood circulation, binding to circulating Aβ. The Aβ-ligand pair can thereafter be cleared from the blood and excreted or degraded via, e.g., hepatic or renal catabolism. In a particular embodiment, the Aβ-ligand is also capable of crossing the blood-brain barrier to some or a significant degree into the cerebroventricular fluid (CVF) in the brain. After binding to soluble Aβ in the CVF, the Aβ-ligand pair can diffuse or be transported into blood, from which it is cleared in the same manner described above. For example, compounds such as insulin-like growth factor 1 (IGF-1), or other compounds having a similar effect, can be used to selectively permeabilize the blood-brain-barrier to transport of Aβ-ligands or complexes between Aβ and a ligand. IGF-1 have been shown to induce clearance of Aβ from the brain in an animal model, which was assumed to be due to an enhanced transport of Aβ carrier proteins such as albumin and transthyretin into the brain (Carro et al., Nat Med 2002; 8:1390-7).

A typical protocol for amyloid dialysis according to any of the embodiments above would comprise selecting a patient who is at risk for or suffers from Alzheimer's Disease, and purifying in vivo or ex vivo bodily fluids of the patient from free Aβ. Specific protocols using the exemplary Aβ-ligand apoE are provided in the Examples. Typically, the dialysis is conducted daily or weekly for as long as necessary for: (i) at least one relevant symptom of Alzheimer's to abate; or (ii) for the level of Aβ peptide in the blood to be reduced or to be significantly undetectable, or some combination thereof.

The efficacy of the treatment can be determined by evaluating the AD symptoms of the patient and/or by measuring the Aβ concentration in the patient's blood. Blood measurements typically involve taking a blood sample, separating serum from red blood cells, and using radioimmunoassay, enzyme linked immunosorbent assay (ELISA) or chromatographic analysis of the Aβ peptide contents in serum.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "hemofiltration" refers to a process of filtering blood by a membrane resulting in the separation of all proteins larger than the effective pore size of the membrane from retained plasma water and solute (these return to the patient) from the ultrafiltrate.

The term "hemofilter" refers to the filter used in hemofiltration. It can be configured in a number of ways, e.g., as a series of parallel plates or as a bundle of hollow fibers. The blood path is from a blood inlet port, through the fibers or between the plates, then on to a blood outlet port. Filtration of blood occurs at the membrane with ultrafiltrate forming on the side of the membrane opposite the blood. This ultrafiltrate accumulates inside the body of the filter contained and embodied by the filter jacket. This jacket has an ultrafiltrate drainage port.

The term "ultrafiltrate" refers to the filtered plasma water and solute and molecules smaller than the effective pore size of the membrane.

The subject or patient to which the present invention may be applicable can be any vertebrate species, preferably mammalian, including but not limited to, cows, horses, sheep, pigs, fowl (e.g., chickens), goats, cats, dogs, hamsters, mice, rats, rabbits, monkeys, chimpanzees, and humans. In a preferred embodiment, the subject is a human. The invention is particularly applicable for human subjects at risk for or suffering from Alzheimer's Disease (AD).

A "control" is an alternative subject or sample used in an experiment for comparison purposes. A control can be "positive" or "negative". For example, where the purpose of the experiment or the comparison in a method is to determine a correlation of an patient treatment with a particular symptom, one may use either a positive control (a patient exhibiting the symptom and not subjected to the treatment, or a sample from such a patient), and/or a negative control (a healthy subject not subjected to the treatment).

As used herein, "treatment" generally refers to a method to reduce the concentration or amount of Aβ in the blood or CVF compartment, including, but not limited to, dialysis or plasma exchange, or the administration of protein or peptides capable of associating in vivo with Aβ in bodily fluids. "Treatment" also includes prophylactic treatment to those at risk for amyloid diseases, i.e., familial Alzheimer's disease.

The term "bodily fluid" as used herein includes blood, plasma, serum, cerebroventricular fluid, cerebrospinal fluid, and other extracellular or interstitial fluids in the body of a subject.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription and Translation* (B. D. Hames & S. J. Higgins, eds. (1984)); *Animal Cell Culture* (R. I. Freshney, ed. (1986)): *Immobilized Cells and Enzymes* (IRL Press, (1986)); B. Perbal, *A practical Guide To Molecular Cloning* (1984); F. M. Ausubel et al. (eds.), *Current Protocols in Molecular Biology*, John Wiley & Sons, Inc. (1994).

Molecular Biology

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense strands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracile, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivitized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "promoter" or "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences.

Promoters which may be used to control gene expression include, but are not limited to, cytomegalovirus (CMV) promoter (U.S. Pat. No. 5,385,839 and No. 5,168,062), the SV40 early promoter region (Benoist and Chambon, Nature 1981; 290:304-310), the promoter contained in the 3' long terminal repeat of Rous sarcoma virus (Yamamoto, et al., Cell 1980: 22:787-797), the herpes thymidine kinase promoter (Wagner et al., Proc. Natl. Acad. Sci. USA 1981; 78:1441-1445), the regulatory sequences of the metallothionein gene (Brinster et al., Nature 1982; 296:39-42); prokaryotic expression vectors such as the beta-lactamase promoter (Villa-Komaroff, et al., Proc. Natl. Acad. Sci. USA 1978; 75:3727-3731), or the tac promoter (DeBoer, et al., Proc. Natl. Acad. Sci. USA 1983; 80:21-25); see also "Useful proteins from recombinant bacteria" in Scientific American 1980, 242:74-94; promoter elements from yeast or other fungi such as the Gal 4 promoter, the ADC (alcohol dehydrogenase) promoter, PGK (phosphoglycerol kinase) promoter, alkaline phosphatase promoter, and transcriptional control regions that exhibit hematopoietic tissue specificity, in particular: beta-globin gene control region which is active in myeloid cells (Mogram et al., Nature 1985; 315:338-340; Kollias et al., Cell 1986:46:89-94), hematopoietic stem cell differentiation factor promoters, erythropoietin receptor promoter (Maouche et al., Blood 1991; 15:2557), etc.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operatively associated with" transcriptional and translational control sequences in a cell when RNA polymerase transcribes the coding sequence into RNA, particularly mRNA, which is then trans-RNA spliced (if it contains introns) and translated into the protein encoded by the coding sequence.

As used herein, the term "isolated" means that the referenced material is removed from its native environment, e.g., a cell. Thus, an isolated biological material can be free of some or all cellular components, i.e., components of the cells in which the native material is occurs naturally (e.g., cytoplasmic or membrane component). A material shall be deemed isolated if it is present in a cell extract or if it is present in a heterologous cell or cell extract. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including without limitation preparative solid phase chromatography, oligonucleotide hybridization, and triple helix chromatography), ultracentrifugation, and other means. Polypeptides and proteins can be purified by various methods including, without limitation, preparative disc-gel electrophoresis and isoelectric focusing; affinity, HPLC, reversed-phase HPLC, gel filtration or size exclusion, ion exchange and partition chromatography; precipitation and salting-out chromatography; extraction; and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting (FACS)). Other purification methods are possible and contemplated herein. A purified material may contain less than about 50%, preferably less than about 75%, and most preferably less than about 90%, of the cellular components, media, proteins, or other nondesirable components or impurities (as context requires), with which it was originally associated. The term "substantially pure" indicates the highest degree of purity which can be achieved using conventional purification techniques known in the art.

The term "express" and "expression" means allowing or causing the information in a gene or DNA sequence to become manifest, for example producing RNA (such as rRNA or mRNA) or a protein by activating the cellular functions involved in transcription and translation of a corresponding gene or DNA sequence. A DNA sequence is expressed by a cell to form an "expression product" such as an RNA (e.g., a mRNA or a rRNA) or a protein. The expression product itself, e.g., the resulting RNA or protein, may also said to be "expressed" by the cell.

The term "expression system" means a host cell and compatible vector under suitable conditions, e.g. for the expression of a protein coded for by foreign DNA carried by the vector and introduced to the host cell. Common expression systems include E. coli host cells and plasmid vectors, insect host cells such as Sf9), Hi5 or S2 cells and Baculovirus vectors, Drosophila cells (Schneider cells) and expression systems, fish cells and expression systems (including, for example, RTH-149 cells from rainbow trout, which are available from the American Type Culture Collection and have been assigned the accession no. CRL-1710) and mammalian host cells and vectors.

The term "transfection" means the introduction of a foreign nucleic acid into a cell. The term "transformation" means the introduction of a "foreign" (i.e., extrinsic or extracellular) gene, DNA or RNA sequence into a host cell so that the host cell will express the introduced gene or sequence to produce a desired substance, in this invention typically an RNA coded by the introduced gene or sequence, but also a protein or an enzyme coded by the introduced gene or sequence. The introduced gene or sequence may also be called a "cloned" or "foreign" gene or sequence, may include regulatory or control sequences (e.g., start, stop, promoter, signal, secretion or other sequences used by a cell's genetic machinery). The gene or sequence may include nonfunctional sequences or sequences with no known function. A host cell that receives and expresses introduced DNA or RNA has been "transformed" and is a "transformant" or a "clone". The DNA or RNA introduced to a host cell can come from any source, including cells of the same genus or species as the host cell or cells of a different genus or species.

The terms "vector", "cloning vector" and "expression vector" mean the vehicle by which a DNA or RNA sequence (e.g., a foreign gene) can be introduced into a host cell so as to transform the host and promote expression (e.g., transcription and translation) of the introduced sequence. Vectors may include plasmids, phages, viruses, etc. and are discussed in greater detail below.

Amyloid-Beta (Aβ) Peptides

Aβ is a 4.1-4.3 kD hydrophobic peptide that is encoded on chromosome 21 as part of a much longer amyloid precursor protein APP (Muller-Hill et al., Nucleic Acids Res 1989:17: 517-522). The APP protein starts with a leader sequence (signal peptide), followed by a cysteine-rich region, an acidic-rich domain, a protease inhibitor motif, a putative N-glycosylated region, a transmembrane domain, and finally a small cytoplasmic region. The Aβ sequence begins close to the membrane on the extracellular side and ends within the membrane. Two-thirds of Aβ faces the extracellular space, and the other third is embedded in the membrane (Kang et al., Nature 1984; 325:733-736, 1987 and Dyrks et al., EMBO J. 1988; 7:949-957). Several lines of evidence suggest that amyloid may play a central role in the early pathogenesis of AD (Soto et al., 1994; 63:1191-1198).

The present invention provides methods of treating an individual suffering from an amyloid disease by removing Aβ present in the individuals bloodstream or other bodily fluid. According to one embodiment of the invention, compounds associated with Aβ (hereinafter alternatively referred to as "binding compounds"), or fragments of such compounds, are administered to a patient suffering from or at risk for an amyloid disease. Such binding compounds are described below.

Aβ Binding Compounds

Aβ "binding compounds" or Aβ "ligands" herein are molecules that bind to Aβ, including Aβ1-40 and Aβ1-42. Exemplary ligands are listed in Table 1, and also include monoclonal antibodies or fragments thereof, synthetic ligands, and the like, and which specifically bind Aβ.

Non-limiting examples of the Aβ binding compounds or ligands for use in present invention are apolipoprotein E, apolipoprotein J, serum amyloid P component, RNA aptamers directed against Aβ, α1-antichymotrypsin, proteoglycans, gangliosides (such as monosiologanglioside GM1), vitronectin, vimentin, and combinations thereof. These are shown in Table 1 below along with commercial sources for the ligands.

TABLE 1

| Amyloid-β binding compound | Company | Source |
|---|---|---|
| Serum Amyloid P | Biogenesis | Human serum |
| α 1-antichymotrypsin | Biodesign, USBio, Biogenesis, ICN, Cortex, Scipac | Human plasma |
| Apolipoprotein E | ICN, USBio, Biodesign, Fitzgerald, Biogenesis, Cortex | Human plasma, human recombinant |
| Vitronectin | Calbiochem, Chemicon Promega, Sigma, | Human plasma |
| Apolipoprotein E4 | ICN | Human recombinant |
| Apolipoprotein E3 | ICN | Human recombinant |
| Apolipoprotein E2 | Biogenesis | Human recombinant |
| Apolipoprotein J | Quidel | Human, purified |
| Heparan Sulfate Proteoglycan | Sigma | Mouse sarcoma |
| Monosiologanglioside GM1 | Sigma | Bovine brain |
| Monosiologanglioside GM2 | Sigma | Bovine brain |
| Monosiologanglioside GM3 | Sigma | Bovine brain |
| Disialoganglioside GD1a | Sigma | Bovine brain |
| Disialoganglioside GD1b | Sigma | Bovine brain |
| Trisialoganglioside GT1b | Sigma | Bovine brain |
| Gangliosides mixture | Sigma | Bovine brain |
| Vimentin | Sigma, Biodesign, Biogenesis | Bovine lens |
| Human serum albumin | ICN, Sigma, Biogenesis | Human serum |
| Human transthyretin | Biogenesis, Sigma | Human plasma |

In addition to these sources, the compounds listed in Table 1 can be purified from human plasma and/or various human tissues. Moreover, proteinaceous compounds can be produced recombinantly using expression systems known to those of ordinary skill in the art disclosed above and the DNA sequences set forth in public databases (World-Wide Web at ncbi.nlm.nih.gov/LocuLink/). The recombinant proteins can be purified using standard techniques well known to those of ordinary skill in the art disclosed above.

One or more of the compounds may also be conjugated to a second moiety. The moiety can be a molecule that prevents degradation and/or increases half-life, reduces toxicity, reduces immunogenicity, facilitates transport over the blood-brain-barrier, or increases biological activity of the Aβ ligand. Exemplary vehicles include human serum albumin or any natural or synthetic protein or polypeptide, an Fc domain (see, e.g., U.S. Pat. No. 6,660,843); a linear polymer (e.g., polyethylene glycol (PEG), polylysine, dextran, etc.); a branched-chain polymer (see, for example, U.S. Pat. Nos. 4,289,872 and 5,229,490 or PCT publication WO 93/21259); a lipid; a cholesterol group (such as a steroid); a carbohydrate or oligosaccharide. The ligand may be conjugated to the second moiety directly or via a linker. See U.S. Pat. No. 6,660,843 for general descriptions of useful conjugation techniques.

Those of ordinary skill in the art will also appreciate that mimetics of these Aβ binding compounds can be used. For example, when the compound has a peptide backbone, the peptide bonds can be replaced with non-peptide bonds. Peptidomimetics can have various different structures (Ripka et. al., Curr. Opin. Chem. Biol. 1998:2:441-452). For example, peptidomimetics can be: (1) peptide analogues containing one or more amide bond replacements (Spatola, A. F., In Chem. Biochem. Amino Acids, Pept., Proteins; Weinstein, B., Ed.; Marcel Dekker: New York, 1983; pp 267-257); (2) peptide analogues with various conformational restraints (Hart, P. A.; Rich, D. H., In Pract. Med. Chem.; Wermuth, C., Ed.; Acad. Press: London, U.K., 1996; pp 393-412), (3) novel structures that replace the entire peptide backbone while retaining isosteric topography of the peptide (Farmer, P. S., In Drug Design; Ariens, E. J., Ed.; Academic Press: New York, 1980; Vol. 10, pp 119-143), and (4) various heterocyclic natural products or screening leads that mimic the function of the natural peptide (Fletcher, M. D. and Campbell, M. M., Chem. Rev. 1998; 98:763-795).

RNA aptamers directed against Aβ can be used to treat amyloid disease pursuant to the present invention. RNA aptamers directed against Aβ are high affinity ligands selected from a combinatorial library described in Ylera et al. (Biochem. Biophys. Res. Comm. 2002:200:1583-1588). Such RNA aptamers can be isolated as disclosed in Ylera et al. (supra) or can be chemically synthesized since Ylera et al. provide the nucleotide sequence of a number of Aβ specific RNA aptamers.

The term "fragment" as used herein refers to the compounds of the present invention which are peptides containing less than the full amino acid sequence of the active parent protein but retain their binding activity to Aβ. Fragments or their mimetics can be detected by standard ELISA-based binding assays (Tokuda et al., Biochem J. 2000:348:359-65); phage display techniques (Rodi et al., Curr Opin Biotechnol 1999:10(1):87-93); yeast two hybrid systems (Uetz P., Curr Opin Chem Biol 2002; 6(1):57-62), and/or protein microarray technology (Templin et al., Trends Biotechnol 2002; 20(4):160-6). These assays can also be used to screen for novel Aβ binding compounds.

Antibodies

In an alternative embodiment, the Aβ ligand or Aβ binding compound is an antibody. The antibodies useful herein can be polyclonal or monoclonal, native or engineered in any suitable manner, and are selective for the particular target molecule. Such antibodies are conveniently made using the methods and compositions disclosed in Harlow and Lane, Antibodies, A Laboratory Manual, Cold Spring Harbor Laboratory, 1988, as well as immunological and hybridoma technologies known to those skilled in the art.

The term "antibody" is intended to include immunoglobulins of all isotypes and species. The antibody can be of can be any type, e.g., an IgG, IgE, IgM, IgD or IgA, preferably, the antibody is an IgG. In another specific embodiment, the construct is derived from a T-lymphocyte receptor. Additionally, the antibody may be of any subclass or isotype of each particular class of antibodies.

A "monoclonal antibody" is an immunoglobulin secreted by a single clone of cells. Any technique that provides for the production of antibody molecules by continuous cell lines in culture may be used. These include but are not limited to the hybridoma technique originally developed by Köhler and Milstein (Nature 1975; 256:495-497), as well as the trioma technique, the human B cell hybridoma technique (Kozbor et al., Immunology Today 1983:4:72 et seq.; Cote et al., Proc. Natl. Acad. Sci. USA 1983; 80:2026-2030), and the EBV hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ free animals (see International PCT Publication WO 89/12690). Particular isotypes of monoclonal antibodies can be prepared either directly by selecting from the initial fusion, or prepared secondarily, from a parental hybridoma secreting a monoclonal antibody of different isotype by using the sib selection technique to isolate class switch variants (Steplewski et al., Proc. Natl. Acad. Sci. USA 1985; 82:8653 et seq.; Spira et al., J. Immunol. Meth. 1984; 74:307 et seq.).

Fragments of an immunoglobulin family protein that are specific to a target molecule can also be prepared. For example, such fragments include but are not limited to: $F(ab')_2$ fragments that contain the variable regions of both the heavy and the light chains, the light constant region and the CH1 domain of the heavy chain, which fragments can be generated by pepsin digestion of an antibody; Fab' fragments: Fab fragments generated by reducing the disulfide bonds of an $F(ab')_2$ fragment (King et al., Biochem. J. 1992; 281:317 et seq.); and Fv fragments, i.e., fragments that contain the variable region domains of both the heavy and light chains (Reichmann and Winter, J. Mol. Biol. 1988; 203:825 et seq.; King et al., Biochem J. 1993; 290:723 et seq.).

Single chain antibodies (SCA) may also be prepared (U.S. Pat. No. 4,946,778; Bird, Science 1988; 242:423-426; Huston et al., Proc. Natl. Acad. Sci. USA 1988; 85:5879-5883; and Ward et al., Nature 1989:334:544-546). Single chain antibodies are formed by linking the heavy and light chain fragments of the Fv region via an amino acid bridge, resulting in a single chain polypeptide. Additionally, the invention also provides heavy chain and light chain dimers and diabodies.

Modified chimeric or humanized antibodies may also be prepared. A chimeric antibody is a molecule in which different portions of the antibody molecule are derived from different animal species, such as those having a variable region derived from a murine monoclonal antibody and a constant region derived from a human immunoglobulin constant region. Techniques have been developed for the production of chimeric antibodies (Morrison et al., Proc. Natl. Acad. Sci. USA 1984; 81:6851-6855; Neuberger et al., Nature 1984; 312:604-608; Takeda et al., Nature 1985; 314:452-454; Oi et al., BioTechniques, 1986:4:214 et seq.; and International Patent Application No. PCT/GB85/00392) by splicing the genes from a mouse antibody molecule of appropriate antigen specificity together with genes from a human antibody molecule of appropriate biological activity. In a specific embodiment, the chimeric antibody contains the variable domain of a non-human antibody and the constant domain of a human antibody. In another embodiment, the construct is derived from a humanized antibody, in which the CDRs of the antibody (except for the one or more CDRs containing the heterologous binding sequence) are derived from an antibody of a non human animal and the framework regions and constant region are from a human antibody (see, U.S. Pat. No. 5,225,539; and Oi et al., supra). The creation of completely human monoclonal antibodies is possible through the use of transgenic mice in which the mouse immunoglobulin gene loci have been replaced with human immunoglobulin loci to provide in vivo affinity-maturation machinery for the production of human immunoglobulins.

Formulation

The present invention also provides methods of using pharmaceutical compositions of the Aβ ligands described herein. Such pharmaceutical compositions may be for administration for injection, or for oral, pulmonary, nasal, transdermal or other forms of administration. In general, the invention encompasses pharmaceutical compositions comprising effective amounts of an Aβ ligands together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form. Implantable sustained release formulations are also contemplated, as are transdermal formulations.

Also contemplated herein is pulmonary delivery of the present A B ligands. The Aβ ligand is delivered to the lungs of a mammal while inhaling and traverses across the lung epithelial lining to the blood stream. (Other reports of this include Adjei et al., Pharma. Res. 1990; 7:565-9; Adjei et al., Internatl. J. Pharmaceutics 1990; 63:135-44 (leuprolide acetate); Braquet et al., J. Cardiovasc. Pharmacol. 1989; 13(suppl.5):s.143-146 (endothelin-1); Hubbard et al., Annals Int. Med. 1989; 3:206-12 (.alpha.1-antitrypsin); Smith et al., J. Clin. Invest. 1989; 84:1145-6 (.alpha.1-proteinase); Oswein et al. (March 1990), "Aerosolization of Proteins", Proc. Symp. Resp. Drug Delivery II, Keystone, Colo. (recombinant human growth hormone); Debs et al. (1988), J. Immunol. 140: 3482-8 (interferon-65 and tumor necrosis factor .alpha.) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn 11 nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass. All such devices require the use of formulations suitable for the dispensing of the Aβ ligand. Typically, each formulation is specific to the type of device employed and may involve the use of an appropriate propellant material, in addition to diluents, adjuvants and/or carriers useful in therapy. The inventive compound should most advantageously be prepared in particulate form with an average particle size of less than 10 .mu.m (or microns), most preferably 0.5 to 5 μm, for most effective delivery to the distal lung.

Pharmaceutically acceptable carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. PEG may be used (even apart from its use in derivatizing the protein or analog). Dextrans, such as cyclodextran, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers known in the art, is contemplated.

In Vivo Treatment

Treatment in vivo, i.e., by a method where an Aβ-binding compound is administered to the patient, is expected to result in reduced amyloid burden within the brain of an Alzheimer's patient and has the potential to halt or slow the progression of the cognitive impairments observed in the disease. In other amyloid diseases, this treatment approach is expected to enhance clearance of the respective amyloid proteins from their target organs in a similar manner and therefore improve the condition of those patients.

Following administration, the compound will bind to Aβ. The Aβ is preferably, although not necessarily, soluble Aβ. The Aβ is free, e.g, not irreversibly bound to an amyloid plaque or other component. Free Aβ includes, but is not limited to, circulating Aβ in blood; free Aβ in the interstitial fluid in the brain; and Aβ bound to a ligand such as a naturally occurring plasma protein, e.g., albumin or transthyretin. In this embodiment, the compound preferably has a higher affinity to Aβ than the plasma protein, so that Aβ preferentially binds the administered compound. Normally, equilibrium is presumed to exist between free Aβ in circulation and Aβ within the brain or other affected organs. A reduction in free Aβ in the circulation by administration of an Aβ ligand which does not cross the blood-brain-barrier can therefore result in an efflux of Aβ out of the brain or other similarly affected organs to re-establish the equilibrium. The bound Aβ will be broken down in the liver and excreted. The subsequent reduction in Aβ within, e.g., the brain leaves less Aβ available for aggregation/fibril formation.

In one embodiment, the patient is treated in a manner so as to increase the selective permeability of the blood-brain barrier, allowing the transport of a particular Aβ ligand into the brain from the blood. In this embodiment, the level of Aβ in the brain can be reduced as the Aβ-ligand complex is transported back into the blood circulation. Treatments to selectively increase the permeability of the blood-brain-barrier to certain Aβ binding compounds in a patient include, but are not limited to, the administration of about 1 to about 1000 μg/kg body weight, preferably about 10 to about 100 μg/kg bodyweight, of IGF-1 as a bolus injection to a patient about 0.5 to 10 hours, preferably about 1 hour, before administration of Aβ binding compounds. While not being bound to any specific theory, this treatment can enhance selective endocytosis of large molecules such as Aβ binding proteins (Carro et al., Nature Med 2002; 8:1390-1397). Also, even without selective permeabilization with a drug such as IGF-1, the blood brain barrier may be compromised in Alzheimer's disease so that Aβ-binding compounds that normally do not enter the brain, or have a saturated uptake, may access the brain more readily. Hence, Aβ clearance mediated by these compounds may be partially from within the brain. Aβ bound to its binding compound or carrier may be shuttled out of the brain or be degraded within the central nervous system. The net effect will be a reduced concentration of Aβ within the interstitial fluid.

The compounds of the present invention may be administered systemically. The term "systemic" as used herein includes parenteral, topical, oral, spray inhalation, rectal, nasal and bucal administration. The term "parenteral" as used herein includes subcutaneous, intravenous, intramuscular, and intraperitoneal administration. Preferably, the compositions are administered orally or intravenously in effective amounts to treat the amyloid diseases.

The specific dosage regimen and amounts administered involved in a method for treating the above-described conditions will be determined by the attending physician, considering various factors which modify the action of drugs, e.g. the age, condition, body weight, sex and diet of the patient, the severity of any infection, time of administration and other clinical factors. An effective amount to treat the diseases would broadly range between about 0.1 mg and about 10 mg per kg body weight of the recipient per day and may be administered as a single or divided doses. Specifically, the amount administered would range between about one-tenth and up to about two-fold of mean plasma levels of the Aβ binding compound. The amount administered of any of the compounds would be no greater than needed to bind all free Aβ in plasma. The treatments can be continued throughout the life of the patient.

The approximate naturally occurring plasma concentrations of Aβ binding compounds and soluble Aβ (sAβ) are as follows:

TABLE 2

| Proteins/Peptides | Mean Plasma Levels (μg/ml) |
| --- | --- |
| Apolipoprotein E (monomer) | 54 |
| Apolipoprotein E (dimer) | 54 |
| Apolipoprotein J | 100 |
| α 1-antichymotrypsin | 40 |
| serum amyloid P component | 34 |
| sAβ | .001 |

Dialysis

In an alternative embodiment, a reduction in free Aβ is achieved not by administering the compounds to the patient but by dialyzing a patient's blood through a column and/or membrane to remove the Aβ protein from the patient's blood. The column or membrane may contain the amyloid-binding compounds of the present invention covalently attached thereto. Using this approach, the patient will not be directly exposed to these endogenous compounds. The reduction of free Aβ as a result of dialysis will result in an efflux of Aβ out of the brain or similarly affected organs in order to re-establish the equilibrium. The subsequent reduction in free Aβ by virtue of dialyzation leaves less Aβ available for aggregation/fibril formation. Similar to the above described in vivo treatment method, this ex vivo treatment method is expected to result in reduced amyloid burden within the brain of an Alzheimer's patient and has the potential to halt or slow the progression of the cognitive impairments observed in the disease.

The dialyzing blood treatments of the invention can be used to reduce or eliminate the presence of specific Aβ peptides free flowing in plasma. Dialysis eliminates the concerns over adverse immune response or other adverse responses to synthetic constructs or monoclonal antibodies because such constructs or monoclonal antibodies are not introduced into the patient's body. Furthermore, dialysis allows instant initiation and cessation of treatment. Preferred methods of dialysis which may be used in the present invention include, but are not limited to, hemodialysis, plasma exchange, plasma perfusion, and hemofiltration. The latter three technologies do not require Aβ binding compounds. The methods may be conducted on a continuous or batch basis. Treated blood may be returned to the patient concurrently with treatment or following treatment. The blood may be supplemented or reconstituted with components from donated blood, artificial or synthetic components.

Hemodialysis is the most common method used to treat advanced and permanent kidney failure. It consists of two compartments separated by a semi-permeable membrane. One compartment is filled with blood, the other is filled with a solution of certain minerals and water (referred to as the dialysate bath). Normal blood is 90% water. Water molecules will pass through the membrane freely back and forth. Blood also contains white and red blood cells, protein, fat, sugar, minerals and waste products. The red and white blood cells are too large to pass through the membrane so they remain in the blood compartment. The same is true of fat and protein molecules. However, electrolytes, because of their smaller size, pass freely through the membrane in both directions (principle of diffusion). This principle states that particles in a solution of high concentration pass through a semi-permeable membrane into a solution of lower concentration until there is an equal concentration of particles on both sides (concentration gradient). The concentration of electrolytes is adjusted in the bath side to approximate the levels in normal human blood serum. Metabolic waste products (urea, creatinine etc.) in the blood (larger molecules but small enough to pass through the membrane) are removed utilizing the principle of diffusion. When the concentration of the waste products reach the levels of the blood, the bath solution is changed either periodically or continuously.

For use in the present invention, Aβ binding compound are added to the dialysis bath. The semi-permeable membrane will have a molecular weight cutoff at 10,000 Daltons. Soluble free Aβ monomers and dimers in the blood will diffuse into the dialysis bath and bind to the Aβ binding compounds. Thereafter, Aβ will not diffuse back into the blood.

The Aβ binding compound in the dialysis compartment may have a high, moderate, or relatively low affinity for Aβ. Compounds having relatively low affinity include albumin and transthyretin. The Aβ-ligand concentration and incubation time in the dialysis compartment can be optimized for each Aβ-ligand, taking affinity and other relevant physicochemical properties into consideration.

In hemofiltration procedures, the principle used to eliminate the waste products is different. Solute (in most cases the blood) is carried across a semi-permeable membrane in response to a transmembrane pressure gradient (a process known as solvent drag). This mimics what actually happens in the normal human kidney. The rate of the ultrafiltration depends upon blood flow. This is very effective in removal of fluid and middle sized molecules, which are thought to cause uremia.

When this method is used, there is no need for Aβ binding compounds. The membranes that are normally used in this technique allow the passage of molecules with a molecular weight of less than 20,000 Daltons. Filtration across the membrane is convective, which means that it is unidirectional. Therefore, filtered Aβ cannot flow back.

Typical procedures also include plasma perfusion (also known as plasma exchange or plasmapheresis): Plasma is the fluid portion of the blood that allows circulation of red blood cells, white blood cells and platelets. It consists of mainly water and numerous chemical compounds. Plasma exchange involves the separation and removal of the plasma from the blood in order to remove disease substances circulating in the plasma. The red and white blood cells and platelets are returned to the patient, along with a replacement fluid. Plasma exchange is accomplished with a device called a blood cell separator. Centrifuge or membrane filters are used to separate plasma from cellular blood components. Blood is drawn from a patient's arm vein by a needle which is attached to a blood tubing set. After it goes through the blood cell separator, the cellular components are drawn from the compartment and replacement fluid prescribed by the physician is added to the cellular components. The mix is returned to the patient usually through a needle. All the steps mentioned above can be done in an automated, continuous and safe manner.

When plasma perfusion is used pursuant to the present invention, Aβ binding compounds are not needed. This approach involves removing the plasma from the patient, while the blood cells and platelets are returned to the patient with replacement fluid.

A typical protocol for dialysis would comprise selecting patients who have Down's syndrome, mild cognitive impairment or those at risk for Alzheimer's disease and conducting dialysis using as a binding member the compounds or fragments thereof associated with Aβ as defined above. Preferably, the dialysis takes place over a period of 2-3 hours, and is repeated as necessary. Typically, dialysis is conducted every 1-7 days for as long as the concentration of free Aβ in the patient's blood remains high, e.g., above 0.1-0.5 ng/ml (10-50% of mean plasma level).

The efficacy of the treatment can be evaluated by either evaluating the symptoms of the patient or by measuring the concentration or amount of target molecules (Aβ) in the patient's blood. The amount of Aβ in the patient's blood can be determined by enzyme linked immunosorbent assay (ELISA) as described below.

In another preferred embodiment of the present invention, the Aβ binding compounds are immobilized, i.e., fixed so that neither the binding compounds nor the binding pair travel with the blood. Preferably, the binding partner construct is immobilized on a solid support using covalent or affinity binding. Covalent linkage can be achieved using standard cyanogen bromide (CNBr) or other activation techniques (International PCT publication WO 00/74824 by Bristow, European Patent No. 272 792 to Jones, U.S. Pat. No. 5,122,112 to Jones), or a high affinity interaction, such as that between avidin and biotin (International PCT publication WO 00/74824 by Bristow; U.S. Pat. No. 6,251,394 to Nilsson). An antibody binding compound can be attached via its Fc region, if present, to a protein-A column (Kiprov et al., J. Biol. Res. Mod. 1984; 3:341-346; Jones et al, J. Biol. Res. Mod. 1984; 3:286-292; Besa et al., Am. J. Med. 1981; 71:1035-1040; EP Application 172018 of Bensinger; EP Application 079221 of Terman; and U.S. Pat. No. 4,614,513 to Bensinger).

To regenerate the solid support containing the binding compounds after use, bound Aβ may be removed preferably by altering the pH and/or by the use of chaotrophic agents. Since the binding compound is not administered to the patient in this embodiment of the present invention, the binding compound may be an antibody. Such antibodies are commercially available from numerous sources such as Bachem, Biogenesis, Biosource, Calbiochem, Chemicon and Sigma. When the binding partner is an antibody, it may be attached via its Fc region to a solid support or membrane.

The solid support utilized in dialysis devices and methods can be made out of a variety of substances (nitrocellulose, cellulose, nylon, plastic, rubber, polyacrylamide, agarose, poly(vinylalcoholo-co-ethylene), and can be formed in a variety of shapes, including flat dialyzers, semi-permeable membranes, semi-permeable hollow fibers, coils, permeable spheres, dialysis membranes, and plasmapheresis filters, optionally using linker molecules such as PEG (polyethelene glycol) to attach the ligand (as disclosed in WO 00/74824). In a hemofiltration device, the solid supports may be, for example, beads, plates, hollow filters, or any combination thereof. One particular method which can be used in the present invention is designed to remove small, non-protein-bound toxins using hollow-fiber technology as disclosed in U.S. Pat. No. 5,919,369.

In ex vivo dialysis procedures, the binding compounds described herein can be used in amounts sufficient to remove the target molecule (Aβ) completely from the blood or simply to reduce the amount of the molecule in the blood. The precise amount of the constructs to be employed depends on the efficiency of the apparatus used and the expected amounts of target molecule in the blood. The amount of binding partner to be immobilized on the solid support can also vary depending on the affinity between binding partner and target, type of perfusion device, and length of perfusion treatment. These amounts can be determined according to the judgment of the practitioner and each patient's circumstances according to standard clinical techniques. Typically, however, the amount of immobilized binding partner would range between about 50- and about 1000-fold molar excess compared to free Aβ in the blood.

Various designs for hemodialysis and dialysis devices are known and have been described in, e.g., patent literature (see, e.g., U.S. Pat. Nos. 4,824,432; 5,122,112; 5,919,369; and 6,287,516; and PCT applications published as WO 90/15631; WO 00/74824: WO 01/37900; and WO 01/45769).

In addition, patients suffering from amyloid disease can be treated by a combination of methods, i.e., administration of the compounds associated with Aβ of the present invention and dialysis. For example, patients can initially be treated using dialysis to rapidly remove the circulating, free Aβ until the amount is stabilized at about 10-50% of the normal value. Thereafter, the compounds of the present invention can be administered, thereby minimizing the number of invasive dialysis treatments The present invention will be better understood by reference to the following examples, which are provided as exemplary of the invention, and not to limit the scope thereof.

EXAMPLES

Example 1

Binding of ApoE Preparations to Aβ Peptide

In the present Example, the binding of apoE, derived from various sources and in various forms, to Aβ1-40 and Aβ1-42 peptides is evaluated.

Materials and Methods

Synthetic Peptides and Proteins.
The following peptides,

```
                                              (SEQ ID NO: 1)
DAEFRHDSGYEVHHQKLVFFAEDVGSNKGAIIGLMVGGVV,
and
                                              (SEQ ID NO: 2)
DAEFRHDSGYEVHHQKLVFFAEDVGSNKGAIIGLMVGGVVIA
``` corresponding to Aβ40 and Aβ42, and identical to residues 672-711 and 672-713 of Aβ-precursor protein 770, respectively, were synthesized at the W.M. Keck Facility at Yale University (New Haven, Conn., U.S.A.) using N-t-butyloxycarbonyl chemistry and purified by HPLC. Aliquots of the final products were lyophilized and stored at −20° C. until use. For preparation of aggregated peptides, 50 μg of either Aβ40 or Aβ42 were dissolved in 100 μl of PBS (0.02 M phosphate buffer, pH 7.4, containing 0.15 M NaCl) and incubated at 37° C. for 72 h. ApoE3 and apoE4 produced in Sf9 insect cells by the *baculovirus* expression system were purchased from PanVera (Madison, Wis., U.S.A.). In all cases, protein purity was corroborated by SDS/PAGE and N-terminal sequence analysis.

ApoE Expressed by Eukaryotic Cell Lines.

Human apoE3 or apoE4 were expressed individually in RAW 264 mouse macrophage cells (A.T.C.C. TIB71) stably transfected with genomic DNA encoding the human apoE isoforms, and in human embryonic kidney (HEK) 293 cells (A.T.C.C. CRL1573) stably transfected with cDNA encoding the human apoE isoforms, and harvested in serum-free conditioned medium for each cell line as described (LaDu et al., J Biol Chem 1994; 269:23403-6; LaDu et al., J Biol Chem 1995; 270:9039-42; Smith et al., J Biol Chem 1988; 263: 8300-8; Miyata et al., Nat Genet. 1996; 14:55-61). Concentrations of secreted apoE were determined by capture-ELISA (ApoTek ApoE: PerImmune, Rockville, Md., U.S.A.) after incubating the harvested conditioned media with 0.05% β-octyl glucopyranoside for 1 h. Aliquots of conditioned media containing apoE3 or apoE4 were stored at 4° C. and used within 2 weeks of harvesting.

Purification of apoE from RAW-264-Cell Conditioned Media.

Polyclonal AB947 anti-apoE antibody (1 ml; Chemicon, Temecula, Calif., U.S.A.) was coupled to 2 ml of CNBr-activated Sepharose 4B according to the manufacturer's instructions. Conditioned media containing apoE3 or apoE4 was loaded on to the AB947-affinity matrix. Bound apoE was eluted with 0.2M acetic acid, pH 2.2, and immediately neutralized. The elution profile was monitored at 280 nm and the pertinent fractions were pooled and dialysed against 0.02 M Tris/HCl, pH 8.5, containing 0.1 M NaCl.

Isolation of apoE-Containing Particles from HEK-293-Cell Conditioned Media.

Aliquots of serum-free conditioned media from HEK-293 cells stably transfected with human apoE3 or apoE4 cDNA, in which the apolipoproteins constituted approximately 50% of the total protein content, were concentrated 50-fold with Centricon-10 (Amicon; Millipore, Bedford, Mass., U.S.A.) as described previously. Particles that contained apoE3 or apoE4 were isolated from the corresponding concentrated conditioned media by FPLC using tandem Superose 6 HR10/30 columns (Pharmacia, Piscataway, N.J., U.S.A.) equilibrated n 0.02 M sodium phosphage, pH 7.4, containing 0.05 M NaCl, 0.03% EDTA and 0.02% sodium azide.

Delipidation of apoE Isoforms Purified from Conditioned Media of Eukaryotic Cell Lines and from *Baculovirus*-Transfected Sf9 Cells.

When apoE is made recombinantly, it is delipidated. This form of apoE is available commercially. Under physiological conditions or upon incorporation into r-HDL particles it becomes lipidated. ApoE in both forms binds Aβ with high affinity.

ApoE isoforms from RAW-264 and HEK-293 cells, purified as described above, as well as apoE produced in SF) insect cells by the *baculovirus* expression system (PanVera), were delipidated in aqueous state using diethyl ether and ethanol. Briefly, the lipoprotein-containing samples were extracted with an equal volume of a 3:2 (v/v) diethyl ether/ethanol mixture, followed by four subsequent extractions of the aqueous phase with a 3:1 (v/v) diethyl ether/ethanol solution. After the final extraction, the remaining solvent was evaporated under a N2 stream and the apoE concentration determined as described above.

Incorporation of apoE Into Reconstituted High-Density Lipoprotein (rHDL) Particles.

Total lipids were extracted from the human HDL fraction using the following method. Human HDL fractions were isolated by preparative gradient ultracentrifugation of plasma obtained from normal healthy subjects, ages 25-40, after a 10-12 h. fast. The HDL fractions were dialysed extensively at 4° C. against PBS containing 1 mM EDTA, and the total lipid fractions (HDL-lipid) were extracted with a mixture of chloroform and methanol (1:2, v/v) and centrifuged at 1700 g for 5 min. The bottom layer that contained the extracted lipids was collected, dried under a N2 atmosphere, dissolved in chloroform and stored at −70° C. until use. The amount of total cholesterol, total triacylglycerols and phospholipids in the HDL and HDL-lipid fractions were determined enzymically with Sigma (St. Louis, Mo., U.S.A.) diagnostic kits.

Reconstituted apoE-containing HDL particles were prepared as follows. rHDL particles containing apoE were prepared as described using recombinant apoE expressed in *baculovirus*-infected Sf9 cells and the HDL-lipids extracted from human plasma HDL lipoparticles. In a typical experiment, the HDL-lipids (500 µg) were placed in a glass tube, dried under N2 atmosphere, resuspended in 0.01 M Tris/HCl buffer, pH 8, containing 0.15 M NaCl (TBS) and 0.001 M EDTA. After the addition of 280 µg of sodium cholate, the suspension was incubated at 4° C. for 12 h. Subsequently, 500 µg of either Sf9 apoE3 or apoE4 was added to the reaction, incubated at 4° C. for another 12 h, and dialysed extensively at 4° C. against PBS containing 0.01% EDTA. The fractions containing apoE incorporated into lipoparticles (apoE-rHDL) were separated from lipid-free apoE by gel-filtration chromatography using a SUPEROSE 12® column (Pharmacia) equilibrated in 0.02 M phosphate buffer, pH 7.4, containing 0.05M NaCl, 0.03% EDTA and 0.02% sodium azide, at a flow rate of 0.8 ml/min. Collected fractions were analyzed by native PAGE using 4-20% Tris/glycine gels and Western-blot analysis employing a monoclonal anti-apoE antibody (3D12; BioDesign, Kennebunk, Me., U.S.A.). The fractions containing apoE-rHDL were pooled for solid-phase binding studies and the concentration of apoE in the lipoparticles was determined using the ApoTek ApoE system as described above.

rHDL-particles were chemically crosslinked as follows. apoE molecules reconstituted into HDL particles were cross-linked using bis(sulphosuccinimidyl) suberate (BS3). Briefly, BS3 was added to the apoE-rHDL fraction at a concentration of 0.002 M in PBS, incubated at room temperature for 4 h., and the reaction stopped by the addition of 0.03 M Tris/HCl buffer, Ph 7.4. After desalting with Microcon 10 (Amicon, Millipore) and lyophilization, the cross-linked samples were separated by Tris/Tricine PAGE (10% polyacrylamide), transferred on to an Immobilon-P membrane (Millipore) and reacted with monoclonal 3D12 anti-apoE antibody followed by horseradish-peroxidase-conjugated anti-mouse IgG. The Western blot was developed by chemiluminescence using the Super-Signal kit (Pierce, Rockford, Ill., U.S.A.).

Solid-Phase Binding Assays.

The binding of apoE to Aβ species was studied by ELISA using immobilized freshly prepared (non-aggregated) or 72-h-aggregated Aβ40 and Aβ42 and apoE3 or apoE4 isoforms with different degrees of lipidation. Polystyrene microtitre plates (Immulon2; Dynex Technology, Chantilly, Va., U.S.A.) were coated for 2 h. at 37° C. with either fresh or aggregated Aβ40 and Aβ42 (40(0 ng in 100 µl of 0.1 M NaHCO$_3$, pH 9.6, per well). Under these conditions, 10 ng of fresh Aβ40, 9.6 ng of fresh Aβ42, 10.2 ng of aggregated Aβ40 and 10.9 ng of aggregated Aβ42 (representing 2.5, 2.4, 2.6 and 2.7% of the peptide offered, respectively) were coated to the microtitre wells, as determined by a modification of the Quantigold assay (Diversified Biotech, Boston, Mass., U.S.A.) for protein quantification. After blocking with Super-block (Pierce), increasing concentrations of apoE (0-150 nM in TBS; 100 µl per well) were added to the Aβ-coated wells and incubated for 3 h. at 37° C. Bound apoE was detected with monoclonal anti-apoE antibody (3D12, 1:1000) followed by alkaline-phosphatase-conjugated goat F(ab')2 anti-mouse IgG (1:3000; BioSource International, Camarillo, Calif., U.S.A.). The reaction was developed for 30 min. with p-nitrophenyl phosphate in diethanolamine buffer (Bio-Rad, Hercules, Calif., U.S.A.), and quantified at 405 nm on a Microplate Reader (Cambridge Technology, Watertown, Mass., U.S.A.). For Scatchard analysis, bound apoE values were expressed in fmol with the aid of a calibration curve in which known concentrations of apoE coated to microtitre wells (as determined by Quantigold assay) were reacted with 3D12, followed by alkaline-phosphatase-conjugated F(ab')2 anti-mouse IgG under conditions identical with those described above. Under the experimental conditions employed, an excess of apoE was reacted with solid-phase Aβ; therefore, only a small fraction of added ligand bound to the immobilized peptide and the concentration of free ligand was considered equivalent to the total apoE added.

Results

Increasing concentrations (0-150 nM) of various apoE3 preparations were reacted with microtiter ELISA wells coated with non-aggregated Aβ140 or Aβ42 for 3 hours. Bound apoE was detected in all cases, with monoclonal 3D12 anti-apoE antibody followed by alkaline phosphatase-labeled anti-mouse IgG. The results are shown in FIG. 1.

In FIG. 1, (A, D) Binding to Aβ40 and Aβ42, respectively, of Sf9-derived apoE3 and apoE4, both delipidated and upon incorporation into r-HDLs. (B, E) Binding to Aβ40 and Aβ42, respectively, of HEK-derived apoE3 and apoE4 both, in their native HDL particles and following delipidation. (C, F) Binding to Aβ40 and Aβ42, respectively, of RAW-derived apoE3 and apoE4, in the native HDL-particles and following delipidation. Each point represents the mean (±standard deviation) of triplicates.

These results show the high affinity binding of apoE to Aβ. Therefore, apoE, and the other compounds disclosed herein, may be used as Aβ binding compounds for the therapeutic purposes disclosed herein.

Example 2

Elicitation of Anti-Aβ-Antibodies Removing Aβ from Blood

This Example describes immunization of animals with synthetic Aβ-derivatives, with subsequent analysis of Aβ content in brain and blood after in vivo formation of anti-Aβ-antibodies. According to the invention, similar results could be obtained by administering externally produced antibodies against Aβ.

Briefly, mice received their first immunization with $K_6A\beta1$-30-$NH_2(E_{18}E_{19})$ at 10.5-13 months of age (peptide: n=23; vehicle: n=24). The animals were bled prior to vaccination, 3 months following the first injection and at the time of sacrifice at 18 to 21 months. The mice were tested in the radial arm maze, subsequently perfused and their brains processed as described (Sigurdsson et al., Am. J. Pathol. 2001; 159:439-4471) (peptide: n=18; vehicle: n=18).

Materials and Methods

Peptide.

$K_6A\beta1$-30-$NH_2(E_{18}E_{19})$ was synthesized at the Keck Foundation (Yale University, New Haven, Conn.). It consists of the first 30 amino acids of amyloid-β with glutamate substituted for valine and phenylalanine in positions 18 and 19. These substitutions result in a T-cell independent immune response as seen by a high IgM response and low IgG response.

Animals.

The vaccination was performed in the Tg2576 APP mouse model developed by Karen Hsiao and colleagues (Hsiao et al., Science 1996:274:99-1022). These mice develop Aβ plaques as early as at 11 to 13 months of age. The animals were maintained on a 12-hour light-dark cycle, and had access to food and water ad libitum. The animal care was in accordance with institutional guidelines.

Vaccine Administration.

$K_6A\beta1$-30-$NH_2(E_{18}E_{19})$ was supplied as trifluoroacetic acid salt. The immunization procedure was performed as previously described by us (Sigurdsson et al., Am. J. Pathol. 2001; 159:439-4471) which is the same protocol as described by Schenk and colleagues (Schenk et al., Nature 1999; 400: 173-1773) except that the peptide was not incubated overnight at 37° C. before injection. Briefly, the peptide was dissolved in phosphate-buffered saline (PBS) at a concentration of 2 mg/ml and then mixed 1:1 (v/v) with the adjuvant or PBS. Complete Freund's adjuvant was used for the first injection, incomplete Freund's adjuvant for the next three injections, and PBS from the fifth injection forward. The mice received a subcutaneous injection of 100 μl of the mixture (ie, 100 μg/100 μl) followed by a second injection 2 weeks later, and then monthly thereafter. Vaccination using the $K_6A\beta1$-30-$NH_2(E_{18}E_{19})$ peptide started when the mice were 10.5-13 months of age and the mice were sacrificed at 18-21 months of age.

Radial Arm Maze.

Animals were kept in test room throughout the experiment, behind a cover to prevent view of the apparatus and room. Each animal underwent 2 days of adaptation, consisting of 15 minutes of maze exploration (2 subjects at a time), with 3 pieces of fruit loops in each arm. Subjects were exposed to arm doors only on day 2. Animals were food deprived 1 day before the first adaptation session and maintained at approximately ten percent body weight loss. Fruit loops were added to normal diet 5 days before deprivation schedule started. Animals entered and exited the apparatus through the center of the maze. Testing included recording correct and incorrect arms entered. Each trial was initiated by placing the mouse in the center of the maze and all doors into the arms were subsequently opened. After entry into an arm, the animal had to find and eat the reinforcer before the door was reopened to allow the animal to re-enter the center of the maze. Testing ended when all eight arms had been entered and reinforcers eaten. Re-entry into an arm constituted an error. Total number of errors and time to enter all eight arms were recorded. The animals were allowed access to food for up to 3-4 hours daily, depending on their body weight loss. The corners and holes in the maze were cleaned with 95% ethanol after each animal and the arms Antibody Levels.

Antibody levels were determined by 1:500 dilutions of plasma using an enzyme-linked immunosorbent assay (ELISA) as described previously (Jimenez-Huete et al., Alzheimers Reports 1998; 1:41-47) in which Aβ or its derivative is coated onto microtiter wells. The antibodies were detected by a goat anti-mouse IgG linked to a horseradish peroxidase (Amersham Pharmacia Biotech, Piscataway, N.J.) or a goat anti-mouse IgM peroxidase conjugate (Sigma, A8786), and tetramethyl benzidine (Pierce, Rockford, Ill.) was the substrate.

Histology.

Mice were anesthetized with sodium pentobarbital (150 mg/kg, intraperitoneally), perfused transaortically with phosphate buffer and the brains processed as previously described (Sigurdsson et al., Neurobiol. Aging 1996; 17:893-901) The right hemisphere was immersion fixed in periodate-lysine-paraformaldehyde (PLP), whereas the left hemisphere was snap-frozen for measurements of Aβ3 levels using established ELISA methods (Mehta et al., Arch. Neurol. 2000; 57:100-105). Serial coronal sections (40 μm) were cut and every fifth section was stained with 6E10 which recognizes Aβ and stains both pre-amyloid and Aβ plaques (Kim et al., Neurosci Res Comm 1990; 7:113-122). After sectioning, the series were placed in ethylene glycol cryoprotectant and stored at −20° C. until used. Staining was performed as previously described (Sigurdsson et al., Neurobiol. Aging 1996; 17:893-901; Soto et al., Nat Med 1998; 4:822-826). Briefly, sections were incubated in 6E10 (kindly provided by Richard Kascsak, Institute for Basic Research) primary antibody that selectively binds to human Aβ at a 1:1000 dilution. A mouse-on-mouse immunodetection kit (Vector Laboratories, Burlingame, Calif.) was used in which the anti-mouse IgG secondary antibody was used at a 1:2000 dilution. The sections were reacted in 3,3-diaminobenzidine tetrahydrochloride (DAB) with nickel ammonium sulfate (Ni; Mallinckrodt, Paris, Ky.) intensification.

Image Analysis.

Immunohistochemistry of tissue sections was quantified with a Bioquant image analysis system, and unbiased sampling was used (West et al., Trends Neurosci. 1999; 22:51-61). All procedures were performed by an individual blind to the experimental condition of the study. Cortical area analyzed was dorsomedially from the cingulate cortex and extended ventrolaterally to the rhinal fissure within the right hemisphere. The area of the grid was 800×800 µm² and amyloid load was measured in 20 frames per mouse (each: 640× 480 µm²), chosen randomly. The Aβ burden is defined as the percentage of area in the measurement field occupied by reaction product. The number of plaques were also counted and the plaques were divided into three groups based on their size (small: 0.01-50 µm²; medium: 50.01-1000 µm²; large: >1000 µm²).

Data Analysis.

The data for the amyloid burden within the brain were analyzed by a Student's t-test, one-tailed (GraphPad Prism). The radial arm maze data was analyzed by two-way ANOVA repeated measures. Bonferroni post hoc test was used to determine if the mice were learning to run the maze. Correlation was determined by calculating the Pearson r correlation coefficient.

Results

Figure 2:
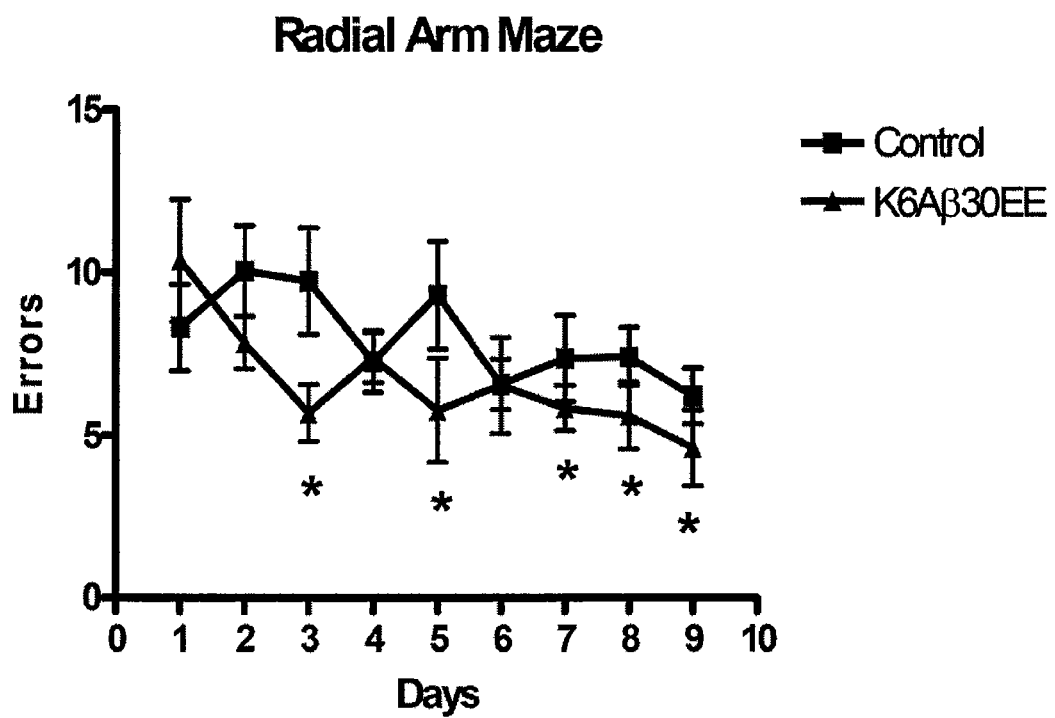
FIG. 2 shows that transgenic mice immunized with $K_6A\beta 1\text{-}30(E_{18}E_{19})$ had significantly fewer errors in the radial arm maze compared to their vehicle-treated controls (two-way ANOVA, repeated measures, p<0.05).

FIG. 2 shows that $K_6A\beta1-30(E_{18}E_{19})$-treated transgenic mice had significantly fewer errors in the radial arm maze compared to their vehicle-treated controls (two-way ANOVA, repeated measures, p<0.05). The mice that were immunized with the peptide showed improvements on days 3, 5, and 7-9 (p<0.01-0.05) compared to their performance on day 1. The control mice did not improve significantly over time.

Figure 3:
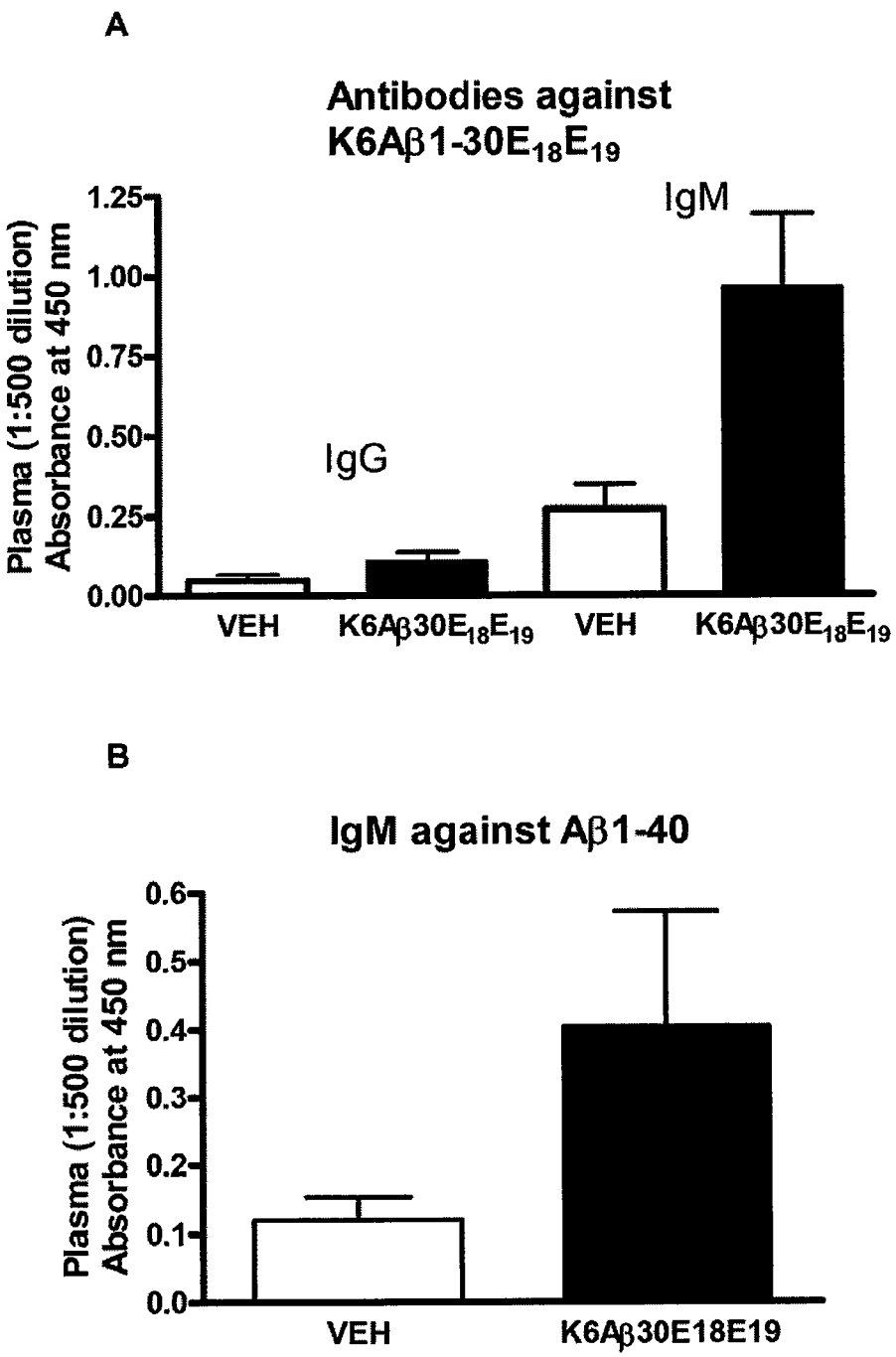
FIG. 3 depicts that (A) $K_6A\beta 1\text{-}30(E_{18}E_{19})$ immunization induced a substantially more pronounced IgM response compared to IgG response as detected in plasma at 1:500 dilution; and that (B) the IgM antibodies generated cross-reacted with Aβ1-40.
Figure 4:
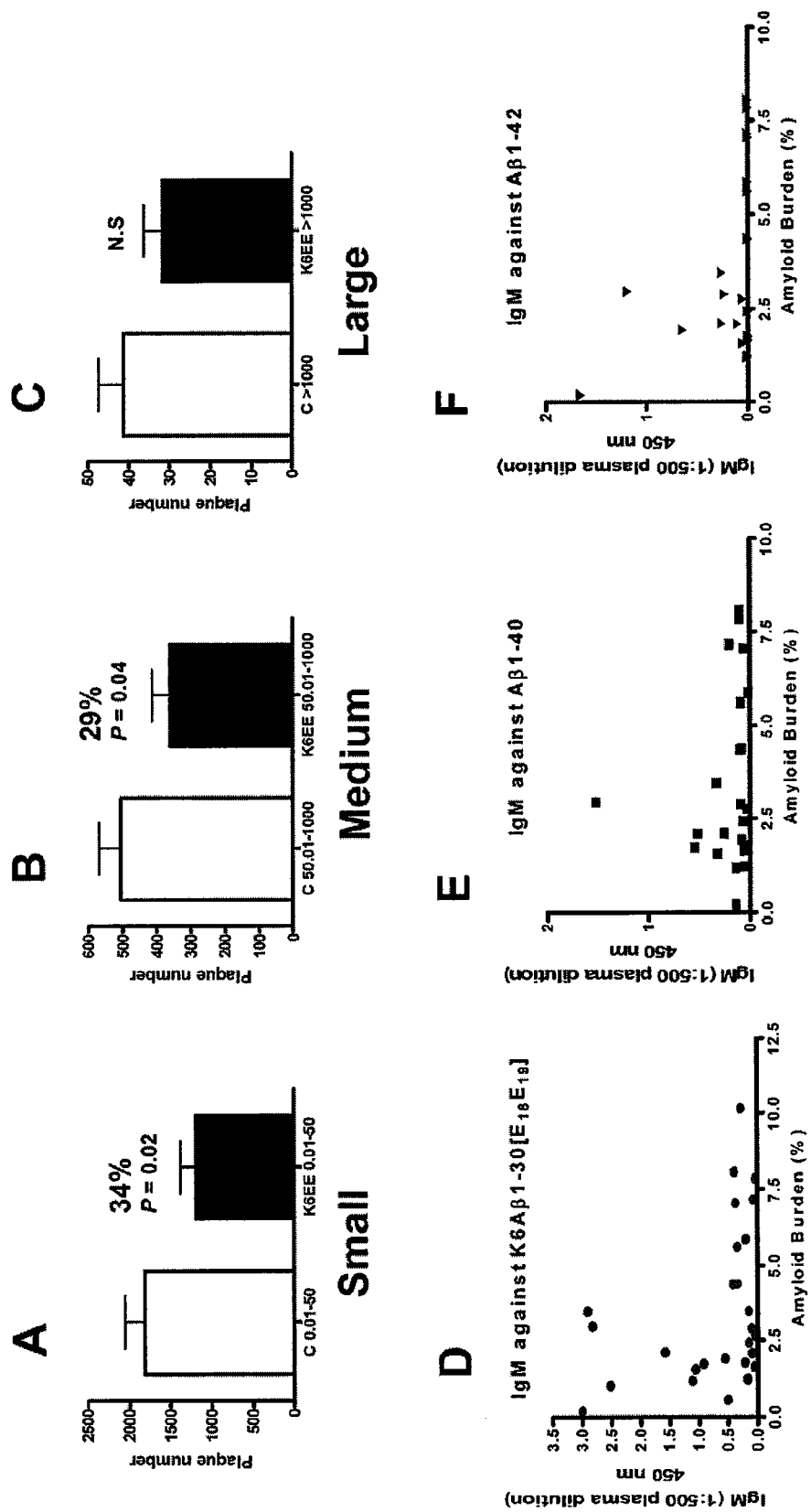
FIGS. 4A-4F show that (A, B, C) $K_6A\beta 1\text{-}30(E_{18}E_{19})$ immunization preferentially reduced small (34% reduction, p=0.02) and medium sized plaques (29% reduction, p=0.04), and that (D, E, F) low amyloid plaque burden correlated with high IgM levels against the immunogen (p<0.05) and Aβ1-42 (p=0.05). A trend for correlation was seen for IgM recognizing Aβ1-40.

FIG. 3 shows that (A) $K_6A\beta1-30(E_{18}E_{19})$ induced a substantially more pronounced IgM response compared to IgG response as detected in plasma at 1:500 dilution: and (B) The IgM antibodies generated following $K_6A\beta1-30(E_{18}E_{19})$ immunization cross-reacted with Aβ1-40.

FIGS. 4A-4F show that (A, B, C) Immunization with $K_6A\beta1-30(E_{18}E_{19})$ preferentially reduced small (34% reduction, p=0.02) and medium sized plaques (29% reduction, p=0.04). Large plaques were not significantly (N.S.) affected. In addition, (D, E, F) low amyloid plaque burden correlated with high IgM levels against the immunogen (p<0.05) and Aβ1-42 (p=0.05). A trend for correlation was seen for IgM recognizing Aβ1-40.

Example 3

Apolipoprotein E3 (ApoE3) Treatment of Patients with Alzheimer's Disease

The present example evaluates the pharmacokinetics and treatment effects of administered ApoE3 versus placebo adjunctive treatment in patients with Alzheimer's disease. Either free, recombinantly produced apoE protein, or apoE protein incorporated into HDL particles can be used in this method. In some cases, apoE incorporated into HDL particles may be preferable, as this is the form apoE is generally found in vivo.

Materials and Methods

The study is a randomized, double blind, placebo controlled parallel group study, and includes patients meeting the following inclusion criteria. Participants must either have genetic mutations that will result in Alzheimer's disease or be diagnosed with the disease, and may be male or female. Parents or guardians will give informed consent for those under the age of 18 years. Exclusion criteria include females who are pregnant or nursing; life-threatening infections; and any condition making participation against the patient's interest.

Patients receive recombinant apoE3 or lipidated recombinant apoE3 as a 1-10 mg/ml solution administered intravenously as a single injection or continuous drip over several minutes daily or weekly. The dose ranges between 0.1 mg and about 10 mg per kg body weight, and the amount administered ranges between about one-tenth and up to about two-fold of mean plasma levels of total apoE. The amount administered is preferably not greater than needed to bind all free Aβ in plasma. Prior to treatment, free plasma Aβ is measured in each patient and the administered dose calculated based on that data and the patients weight, taking into consideration the known pharmacokinetic properties of apoE3.

Briefly, apoE3 is prepared as described in Example 1. Pharmacokinetic sampling is performed with the administration set as time=0. Briefly, blood samples (5 ml) are collected at the following times: baseline, and at 1, 2, 4, 8, 12, and 24 hours and weekly thereafter. Blood samples are collected via catheterization of the antecubical or other readily accessible vein, or by direct venipuncture. Each tube is mixed and immediately iced. Plasma is separated within 2 hours by centrifugation at 1500×g for 15 minutes in a refrigerated (4° C.) centrifuge. All tubes are stored at <−20° C. pending analysis. The samples are analyzed for free and total Aβ levels as well as levels of apoE3. Subsequent dosing will be based on this information with the aim of maintaining very low levels of free Aβ in plasma. Cerebrospinal fluid will be obtained by lumbar puncture at the beginning and end of the study for measurements of total and free Aβ.

The patients are evaluated prior to treatment and every 6 weeks for symptoms of Alzheimer's disease using standard cognitive tests as described by, e.g., Rogers et al., Neurology 1998; 50:136-145. Primary measures are the Alzheimer's Disease Assessment Scale (ADAS-cog) and Clinician's Interview Based Assessment of Change-Plus (CIBIC plus), with Mini-Mental State Examination (MMSE), the Clinical Dementia rating Scale-Sum of the Boxes (SDR-SB) and patient rated Quality of Life (QoL) used as secondary measures. Any available imaging method allowing imaging of amyloid burden in live subjects is used concurrently.

The same method can be used to evaluate other Aβ-binding agents set forth in Table 1, with modifications that are within the level of skill in the art, e.g., to modify the amount of active compound to be present in the plasma so as to compensate for differences in molecular weight between apoE and the agent, and for difference in binding affinity towards Aβ and the agent.

Example 4

Apolinoprotein E3 (ApoE3) Hemodialysis Treatment in Patients with Alzheimer's Disease This Example evaluates the treatment effects in patients with Alzheimer's disease of hemodialysis of Aβ from blood by dialyzing the blood through a membrane with apoE3 added to the dialysate bath versus no treatment or versus hemodialysis without apoE3. Either free, recombinantly produced apoE protein, or apoE protein incorporated into HDL particles can be used in this method, although free apoE protein is preferred due to the more simple preparation procedure.

Materials and Methods

The study is a randomized, double blind, placebo controlled parallel group study, and includes patients meeting the following inclusion criteria. Participants must either have genetic mutations that will result in Alzheimer's disease or have been diagnosed with the disease, and may be male or female. Parents or guardians will give informed consent for those under the age of 18 years. Exclusion criteria include females who are pregnant or nursing; life-threatening infections; and any condition making participation against the patient's interest.

Recombinant apoE3 or lipidated recombinant apoE3 is added to the dialysis bath. The concentration does not necessarily have to be greater or different than that needed to bind all free Aβ that diffuses from the blood compartment of the dialysis unit. Prior to treatment, free plasma Aβ is measured in each patient and the dose added to the dialysate bath calculated based on that data taking into consideration the known affinity of apoE3 for Aβ. ApoE3 is prepared as described in Example 1. The semipermeable membrane has a molecular weight cutoff of 10,000 Daltons. Soluble free Aβ monomers, dimers and oligomers in the blood diffuse into the dialysis bath and bind to apoE3. Thereafter, Aβ does not diffuse back into the blood.

This procedure is performed monthly with blood samples collected at time=0, immediately following dialysis and at 12, 24 hours and weekly thereafter. Blood samples are collected via catheterization of the antecubical or other readily accessible vein, or by direct venipuncture. Each tube is mixed and immediately iced. Plasma is separated within 2 hours by centrifugation at 1500×g for 15 minutes in a refrigerated (4° C.) centrifuge. All tubes are stored at <−20° C. pending analysis. The samples are analyzed for free and total Aβ levels. Subsequent dosing is based on this information with the aim of maintaining very low levels of free Aβ in plasma. Cerebrospinal fluid will be obtained by lumbar puncture at the beginning and end of the study for measurements of total and free Aβ.

The patients are evaluated prior to treatment and every 6 weeks for symptoms of Alzheimer's disease using standard cognitive tests as described by, e.g., Rogers et al., Neurology 1998; 50:136-145. Primary measures are the Alzheimer's Disease Assessment Scale (ADAS-cog) and Clinician's Interview Based Assessment of Change-Plus (CIBIC plus), with Mini-Mental State Examination (MMSE), the Clinical Dementia rating Scale-Sum of the Boxes (SDR-SB) and patient rated Quality of Life (QoL) used as secondary measures. Any available imaging method allowing imaging of amyloid burden in live subjects is used concurrently.

The same method can be used to evaluate other Aβ-binding agents set forth in Table 1, with modifications that are within the level of skill in the art, e.g., to modify the amount of active compound to be present in the dialysis compartment so as to compensate for differences in molecular weight between apoE and the agent.

Example 5

Convective Dialysis Treatment in Patients with Alzheimer's Disease

This Example evaluates the treatment effects in patients with Alzheimer's disease by studying hemofiltration of Aβ from blood by dialyzing the blood through a unidirectional membrane as compared to no treatment.

Materials and Methods

The study is a randomized, double blind, placebo controlled parallel group study, and includes patients meeting the following inclusion criteria. Participants must either have genetic mutations that will result in Alzheimer's disease or have been diagnosed with the disease, and may be male or female. Parents or guardians will give informed consent for those under the age of 18 years. Exclusion criteria include females who are pregnant or nursing; life-threatening infections; and any condition making participation against the patient's interest.

In this method, there is no need for Aβ binding compounds, and the membranes allow the passage of molecules less than 20,000 Daltons. Filtration across the membrane is unidirectional. Therefore, filtered Aβ cannot flow back.

Prior to treatment, free and total plasma Aβ is measured in each patient. Soluble free Aβ monomers, dimers and oligomers in the blood diffuse across the dialysis membrane in response to a transmembrane pressure gradient. Thereafter, Aβ will not diffuse back into the blood.

The procedure is performed monthly with blood samples collected at time=0, immediately following dialysis and at 12, 24 hours and weekly thereafter. Blood samples are collected via catheterization of the antecubical or other readily accessible vein, or by direct venipuncture. Each tube is mixed and immediately iced. Plasma is separated within 2 hours by centrifugation at 1500×g for 15 minutes in a refrigerated (4° C.) centrifuge. All tubes are stored at <−20° C. pending analysis. The samples are analyzed for free and total Aβ levels. The interval between dialysis treatment is based on this information with the aim of maintaining very low levels of free Aβ in plasma. Cerebrospinal fluid will be obtained by lumbar puncture at the beginning and end of the study for measurements of total and free Aβ.

The patients are evaluated prior to treatment and every 6 weeks for symptoms of Alzheimer's disease using standard cognitive tests as described by, e.g., Rogers et al., Neurology 1998; 50:136-145. Primary measures are the Alzheimer's Disease Assessment Scale (ADAS-cog) and Clinician's Interview Based Assessment of Change-Plus (CIBIC plus), with Mini-Mental State Examination (MMSE), the Clinical Dementia rating Scale-Sum of the Boxes (SDR-SB) and patient rated Quality of Life (QoL) used as secondary measures. Any available imaging method allowing imaging of amyloid burden in live subjects is used concurrently.

Example 6

Plasma Exchange Dialysis Treatment in Patients with Alzheimer's Disease

This example evaluates the treatment effects in patients with Alzheimer's disease by removal of Aβ from blood by plasma exchange dialysis versus no treatment.

Materials and Methods

The study is a randomized, double blind, placebo controlled parallel group study, and includes patients meeting the following inclusion criteria. Participants must either have genetic mutations that will result in Alzheimer's disease or have been diagnosed with the disease, and may be male or female. Parents or guardians will give informed consent for those under the age of 18 years. Exclusion criteria include females who are pregnant or nursing; life-threatening infections; and any condition making participation against the patient's interest.

In this method, there is no need for Aβ binding compounds. The plasma is separated and removed from the rest of the blood to remove Aβ circulating in blood. The red and white blood cells and platelets are returned to the patient, along with replacement fluid. Using this method, all Aβ is removed from the blood. Prior to treatment, free and total plasma Aβ would be measured in each patient.

The procedure is performed monthly with blood samples collected at time=0, immediately following dialysis and at 12, 24 hours and weekly thereafter. Blood samples are collected via catheterization of the antecubical or other readily accessible vein, or by direct venipuncture. Each tube is mixed and immediately iced. Plasma is separated within 2 hours by centrifugation at 1500×g for 15 minutes in a refrigerated (4° C.) centrifuge. All tubes are stored at <−20° C. pending analysis. The samples are analyzed for free and total Aβ levels. The interval between dialysis treatment is based on this information with the aim of maintaining very low levels of free Aβ in plasma. Cerebrospinal fluid will be obtained by lumbar puncture at the beginning and end of the study for measurements of total and free Aβ.

The patients are evaluated prior to treatment and every 6 weeks for symptoms of Alzheimer's disease using standard cognitive tests as described by, e.g., Rogers et al., Neurology 1998; 50:136-145. Primary measures are the Alzheimer's Disease Assessment Scale (ADAS-cog) and Clinician's Interview Based Assessment of Change-Plus (CIBIC plus), with Mini-Mental State Examination (MMSE), the Clinical Dementia rating Scale-Sum of the Boxes (SDR-SB) and patient rated Quality of Life (QoL) used as secondary measures. Any available imaging method allowing imaging of amyloid burden in live subjects is used concurrently.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method of treating an amyloid disease in a patient in need of such treatment comprising filtering the blood of the patient through a membrane, filter or column, thereby removing circulating amyloid-beta from the patient and reducing amyloid-beta burden within the brain of the patient, wherein the membrane, filter or column comprises an antibody or antibody fragment which is bound or conjugated to the membrane, filter, or column and which binds to amyloid-beta, and wherein the patient is not exposed directly to said antibody or antibody fragment.

2. The method of claim 1, wherein the filtered blood is returned to said patient.

3. The method of claim 1, wherein the amyloid disease is Alzheimer's disease.

* * * * *